US009803211B2

(12) United States Patent
Peet et al.

(10) Patent No.: US 9,803,211 B2
(45) Date of Patent: Oct. 31, 2017

(54) PROTEIN PRODUCTION IN TRANSGENIC POTATO PLANTS HAVING SUPPRESSED EXPRESSION OF PATATIN AND CD4B

(71) Applicant: J.R. Simplot Company, Boise, ID (US)

(72) Inventors: Richard C. Peet, Washington, DC (US); Caius Rommens, Boise, ID (US); Robert Chretien, Danville, VA (US); Hua Yan, Boise, ID (US); Teruko Osumi, Garden City, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

(21) Appl. No.: 14/897,164

(22) PCT Filed: Jun. 13, 2014

(86) PCT No.: PCT/US2014/042245
§ 371 (c)(1),
(2) Date: Dec. 9, 2015

(87) PCT Pub. No.: WO2014/201321
PCT Pub. Date: Dec. 18, 2014

(65) Prior Publication Data
US 2016/0138033 A1 May 19, 2016

Related U.S. Application Data

(60) Provisional application No. 61/835,274, filed on Jun. 14, 2013.

(51) Int. Cl.
*C12N 15/82* (2006.01)
*A01H 5/04* (2006.01)

(52) U.S. Cl.
CPC ............ *C12N 15/8218* (2013.01); *A01H 5/04* (2013.01); *C12N 15/8251* (2013.01); *C12N 15/8257* (2013.01)

(58) Field of Classification Search
None
See application file for complete search history.

(56) References Cited

U.S. PATENT DOCUMENTS

| 6,057,493 | A | 5/2000 | Willmitzer et al. |
| 8,222,488 | B2 | 7/2012 | Scholthof |
| 8,809,559 | B2 | 8/2014 | Petrie et al. |
| 2002/0046418 | A1 | 4/2002 | Hooker et al. |
| 2002/0108149 | A1 | 8/2002 | Gruis et al. |
| 2006/0156428 | A1 | 7/2006 | Rommens et al. |
| 2009/0144849 | A1 | 6/2009 | Lutfiyya |
| 2011/0289622 | A1 | 11/2011 | Heim et al. |
| 2012/0284871 | A1 | 11/2012 | Lomonossoff et al. |

FOREIGN PATENT DOCUMENTS

| EP | 1074629 A1 | 2/2001 |
| EP | 2080803 A1 | 7/2009 |
| JP | 2012509059 A | 4/2012 |
| WO | WO 92/11376 A1 | 7/1992 |
| WO | WO 02/08382 A2 | 1/2002 |
| WO | 2004085656 A2 | 10/2004 |
| WO | WO 2008/090174 A1 | 7/2008 |
| WO | WO 2010/099462 A2 | 9/2010 |
| WO | WO 2014/201321 A1 | 12/2014 |

OTHER PUBLICATIONS

Kim et al. Development of patatin knockdown potato tubers using RNA interference (RNAi) technology, for the production of human-therapeutic glycoproteins. (2008) BMC Biotechnoloogy; vol. 8; pp. 1-9.*

Clarke et al. The ATP-dependent Clp protease in chloroplasts of higher plants. (2005) Physiologia Plantarum; vol. 123; pp. 406-412.*

Ahn et al. "Host-dependent suppression of RNA silencing mediated by the viral suppressor p19 in potato," Planta. Jun. 30, 2011, pp. 1065-1072, vol. 234.

Daniell et al. "Complete chloroplast genome sequences of Solanum bulbocastanum, Solanum lycopersicum and comparative analyses with other Solanaceae genomes," Theor Appl Genet. Mar. 31, 2006, pp. 1503-1518, vol. 112.

Hoskins et al. "Protein binding and unfolding by the chaperone ClpA and degradation by the protease ClpAP." Proc Nail Acad Sci USA. Aug. 1. 2000, pp. 8892-8897, vol. 97.

Kim et al. "Development of patatin knockdown potato tubers using RNA interference (RNAi) technology, for the production of human-therapeutic glycoproteins," BMC Biotechnol. Apr. 3, 2008, pp. 1-9, vol. 8, No. 36.

Müller-Röber et al. "Inhibition of the ADP-glucose pyrophosphorylase in transgenic potatoes leads to sugar-storing tubers and influences tuber formation and expression of tuber storage protein genes," EMBO J. Apr. 1, 1992 (Apr. 1, 1992), pp. 1229-1238, vol. 11.

Rensink et al. "Analyzing the potato abiotic stress transcriptome using expressed sequence tags," Genome. Aug. 6, 2005 (Aug. 6, 2005), pp. 598-605, vol. 48.

(Continued)

*Primary Examiner* — Cathy Kingdon Worley
(74) *Attorney, Agent, or Firm* — Cooley LLP

(57) ABSTRACT

The present disclosure relates to methods and constructs for producing heterologous peptides and proteins in plants in a safe and controlled manner. One aspect of the present invention provides a method of producing heterologous protein in a transformed potato plant using an expression cassette comprising a gene coding for a protein or peptide of interest and a marker gene, a nucleotide sequence capable of suppressing patatin expression, along with a nucleotide sequence capable of suppressing CD4B expression, and/or a nucleotide sequence capable of overexpressing P19. Another aspect of the invention provides a method of producing a heterologous protein in a transformed potato plant using an expression cassette comprising a gene coding for a protein or peptide of interest, a marker gene, a transit peptide sequence, and a nucleotide sequence capable of suppressing ADP glucose pyrophosphorylase expression.

8 Claims, 29 Drawing Sheets

(56) References Cited

OTHER PUBLICATIONS

Shanklin et al. "The stroma of higher plant plastids contain ClpP and ClpC, functional homologs of *Escherichia coli* ClpP and ClpA: an archetypal two-component ATP-dependent protease," Plant Cell. Oct. 1, 1995 (Oct. 1, 1995), pp. 1713-1722, vol. 7.
International Search Report, PCT/US2014/042245, mailed Apr. 11, 2014, 5 pages.
Office Action (English translation) in corresponding Japanese Application No. 2016-519668 mailed Sep. 30, 2016, 6 pages.
Bhatnagar, Madhurima, et al. "An efficient method for the production of marker-free transgenic plants of peanut (*Arachis hypogaea* L.)." Plant Cell Reports (2010); 29.5: 495-502.
de Almeida, Elionor RP, et al. "Transgenic expression of two marker genes under the control of an Arabidopsis rbcS promoter: Sequences encoding the Rubisco transit peptide increase expression levels." Molecular and General Genetics MGG (1989); 218.1: 78-86.
European Application No. 14810535.6, Extended European Search Report dated Feb. 28, 2017, 17 pages.
European Application No. 14810535.6, Partial Supplementary European Search Report dated Dec. 15, 2016, 9 pages.
International Preliminary Report on Patentability, PCT/US2014/042245, dated Dec. 15, 2015, 8 pages.
Miki, Brian, and McHugh, Sylvia. "Selectable marker genes in transgenic plants: applications, alternatives and biosafety." Journal of Biotechnology (2004); 107.3: 193-232.
Sanjaya et al. "Increasing the energy density of vegetative tissues by diverting carbon from starch to oil biosynthesis in transgenic Arabidopsis." Plant Biotechnology Journal (2011); 9.8: 874-883.
Written Opinion, PCT/US2014/042245, mailed Nov. 4, 2014, 7 pages.

\* cited by examiner

Untransformed

Transformed

PROTEIN PRODUCTION IN TRANSGENIC POTATO PLANTS HAVING SUPPRESSED EXPRESSION OF PATATIN AND CD4B

CROSS-REFERENCE TO RELATED PATENT APPLICATIONS

This application claims priority from Provisional Application U.S. Application 61/835,274, filed Jun. 14, 2013, incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: JRSI_029_04US_SeqList_ST25.txt, date recorded: Apr. 25, 2017, file size 10kilobytes).

FIELD OF THE INVENTION

The present disclosure relates to molecular biology and protein synthesis in plant cells. More specifically, the disclosure provides methods and constructs for producing a peptide or protein of interest in *planta*. All publications cited in this application are herein incorporated by reference.

BACKGROUND OF THE INVENTION

Until recently, pharmaceuticals, such as antibiotics, analgesics and hormones, derived from small organic molecules were mainly produced synthetically or in microbes. However, with the development of genomics and proteomics, new drug therapies involve larger protein molecules. Because proteins play key roles in cell biology and development, many proteins have therapeutic potential.

While short peptide chains of about thirty amino acids can be synthesized, larger proteins are best produced by living cells. Presently, a vast array of large proteins are produced using sterile microbial and mammalian cell cultures. However, because cell culture systems are expensive and laborious to maintain, plant-based expression systems provide lower production costs and more manageable large-scale production.

SUMMARY OF THE INVENTION

It is an object of the present invention to provide methods for producing a heterologous peptide or protein of interest in a potato plant. One aspect of the present invention provides a method of producing heterologous protein in a transformed potato plant comprising the steps of (a) transforming a plant with an expression cassette, the expression cassette comprising (i) a nucleotide sequence capable of suppressing patatin expression, (ii) a nucleotide sequence capable of suppressing CD4B expression, (iii) a marker gene and (iv) a gene coding for a protein or peptide of interest; (b) cultivating the transformed plant under a defined condition; and (c) extracting the protein of interest. Also provided is a method wherein the nucleotide sequence capable of suppressing patatin expression comprises antisense and sense sequences of patatin as set forth in SEQ ID NO:3 and SEQ ID:4. Another method is also provided wherein the nucleotide sequence capable of suppressing CD4B expression comprises antisense and sense sequences of CD4B as set forth in SEQ ID NO:5 and SEQ ID NO:6. The method may also comprise a marker gene selected from a group consisting of GFP, EGFP, GUS, LUX, CAH, SPT, NPTII, HPT, APHIV, BAR, PAT, CHS, AHAS, and flavonoid synthesis genes.

Also provided is a method wherein the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

Another aspect of the present invention is a method of producing heterologous protein in a transformed potato plant comprising the steps of (a) transforming a plant with an expression cassette, the expression cassette comprising (i) a nucleotide sequence capable of suppressing patatin expression, (ii) a nucleotide sequence capable of overexpressing P19, (iii) a marker gene and (iv) a gene coding for a protein or peptide of interest; (b) cultivating the transformed plant under a defined condition; and (c) extracting the protein of interest. Also provided is a method wherein the nucleotide sequence capable of suppressing patatin expression comprises antisense and sense sequences of patatin as set forth in SEQ ID NO:3 and SEQ ID:4. Another method is also provided wherein the nucleotide sequence capable of overexpressing P19 comprises the P19 sequence as set forth in SEQ ID NO:2. The method may also comprise a marker gene selected from a group consisting of GFP, EGFP, GUS, LUX, CAH, SPT, NPTII, HPT, APHIV, BAR, PAT, CHS, AHAS, and flavonoid synthesis genes.

Also provided is a method wherein the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

Another aspect of the present invention is a method of producing heterologous protein in a transformed potato plant comprising the steps of (a) transforming a plant with an expression cassette, the expression cassette comprising (i) a nucleotide sequence capable of suppressing patatin expression, (ii) a nucleotide sequence capable of suppressing CD4B expression, (iii) a nucleotide sequence capable of overexpressing P19, (iv) a marker gene and (v) a gene coding for a protein or peptide of interest; (b) cultivating the transformed plant under a defined condition; and (c) extracting the protein of interest. Also provided is a method wherein the nucleotide sequence capable of suppressing patatin expression comprises antisense and sense sequences of patatin as set forth in SEQ ID NO:3 and SEQ ID:4. A method is also provided wherein the nucleotide sequence capable of suppressing CD4B expression comprises antisense and sense sequences of CD4B as set forth in SEQ ID NO:5 and SEQ ID NO:6. Another method is also provided wherein the nucleotide sequence capable of overexpressing P19 comprises the P19 sequence as set forth in SEQ ID NO:2. The method may also comprise a marker gene selected from a group consisting of GFP, EGFP, GUS, LUX, CAH, SPT, NPTII, HPT, APHIV, BAR, PAT, CHS, AHAS, and flavonoid synthesis genes.

Also provided is a method wherein the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

In an additional embodiment the invention provides a method of producing a heterologous protein in a transformed potato plant comprising the steps of: (a) transforming a plant with an expression cassette, the expression cassette comprising (i) a nucleotide sequence capable of suppressing ADP glucose pyrophosphorylase (AGP) expression; (ii) a transit peptide; (iii) a marker gene; and (iv) a gene coding for a protein or peptide of interest; (b) cultivating the transformed plant under a defined condition; and (c) extracting the protein of interest.

In a preferred embodiment, the nucleotide sequence capable of suppressing AGP expression comprises an antisense or a sense AGP sequence as set forth in SEQ ID:10 and SEQ ID NO:11. Preferably, suppression of AGP expression is driven by convergent promoters. In a preferred aspect of the invention, the convergent promoters are the granular bound starch synthase (GBSS) promoter and the AGP promoter.

Also provided is a method wherein the transit peptide is the GBSS-transit peptide as set forth in SEQ ID NO:8 or the RuBisCo transit peptide as set forth in SEQ ID NO:9. The method of the invention may also comprise a marker gene selected from a group consisting of GFP, EGFP, GUS, LUX, CAH, SPT, NPTII, HPT, APHIV, BAR, PAT, CHS, AHAS, and flavonoid synthesis genes.

Preferably, the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

The foregoing general description and the detailed description are exemplary and explanatory and are intended to provide further explanation of the invention as claimed. For detailed understanding of the invention, reference is made to the following detailed description of the preferred embodiments, taken in conjunction with the accompanying drawing. Other objects, advantages and novel features will be readily apparent to those skilled in the art from the following detailed description of the invention.

SUMMARY OF THE SEQUENCE LISTING

Figure 1:
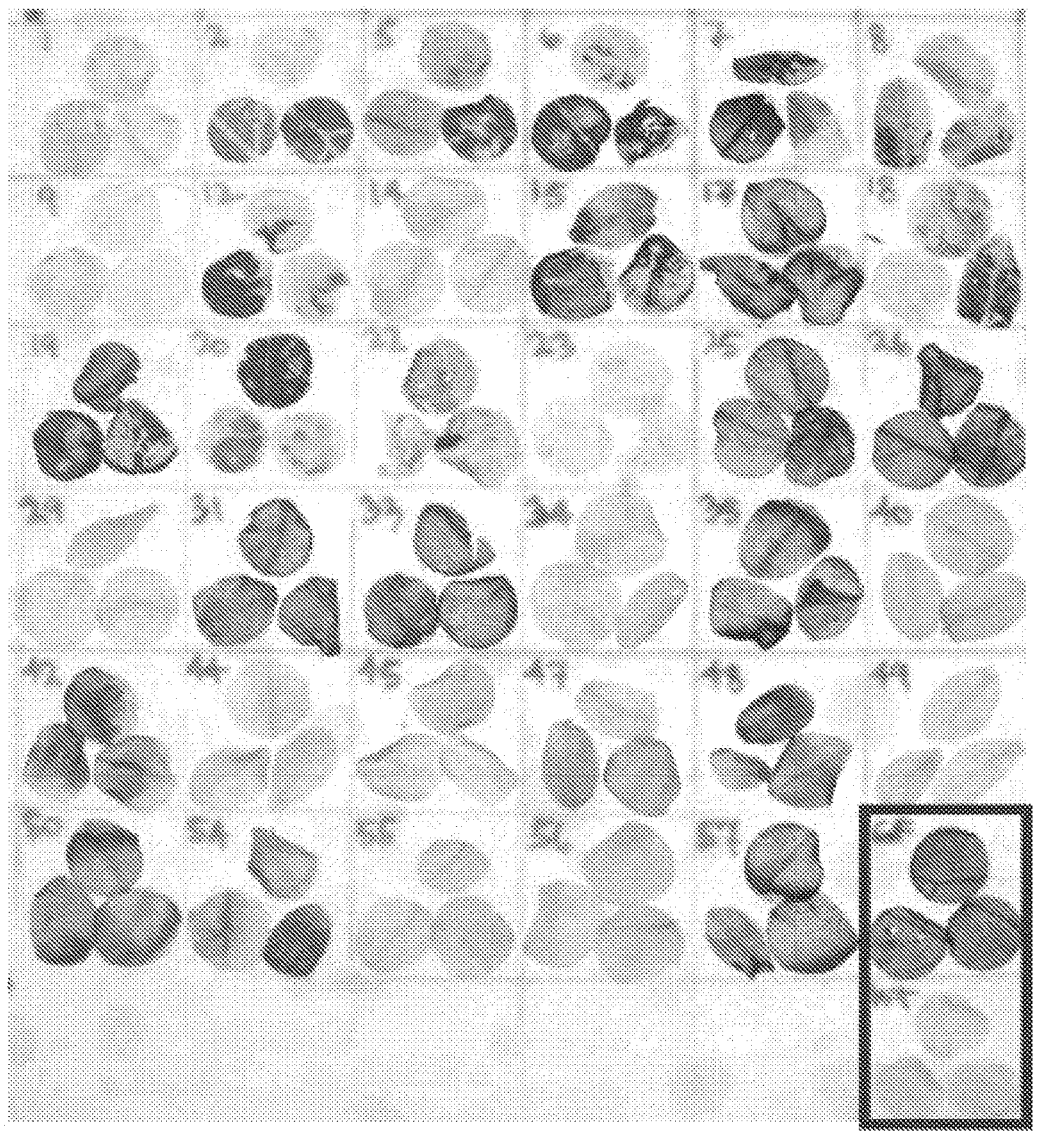
FIG. 1. Histochemically stained tobacco leaf punches of plants containing both the GUS gene and the GUS gene silencing construct pSIM789. Boxed leaf samples depict stained GUS positive control (top) and wild-type (bottom) plants.
Figure 2:
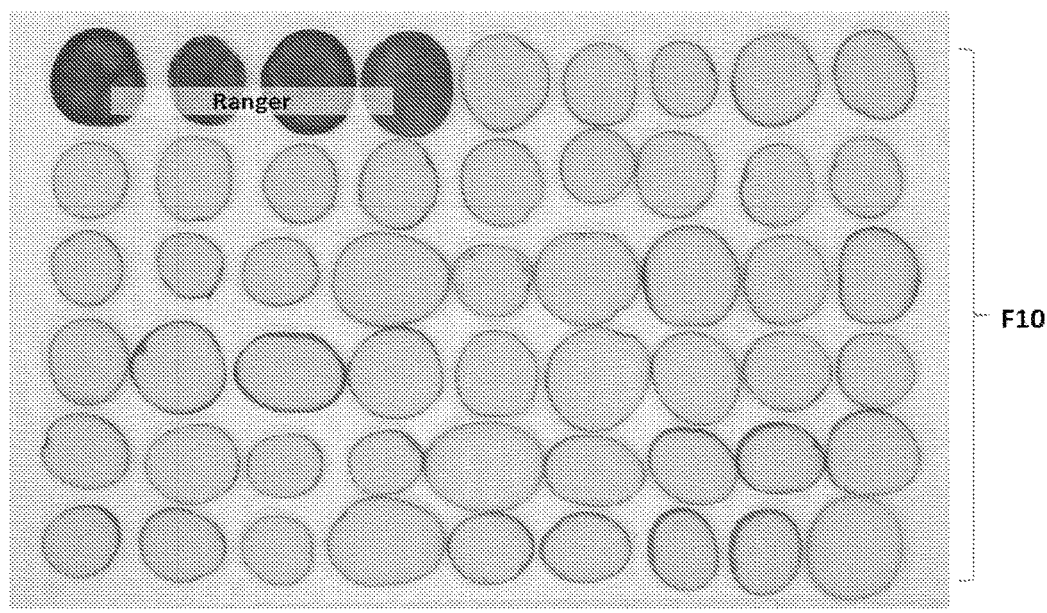
FIG. 2 shows the results of a catechol assay of potatoes. Tubers of the transgenic line F10 containing a silencing construct designed to silence the polyphenol oxidase-5 (PPO5) gene showed reduced polyphenol oxidase-5 activity in as compared to tubers of untransformed control (first four samples on top).

The present application is being filed along with a Sequence Listing in electronic format. The information in the electronic format of the Sequence Listing is part of the present application and is incorporated herein by reference in its entirety.

SEQ ID NO:1 sets forth the sequence of patatin from potato.
SEQ ID NO:2 sets forth the sequence of the P19 mutant P19R43.
SEQ ID NO:3 sets forth the antisense sequence of patatin PATB1.
SEQ ID NO:4 sets forth the sense sequence of patatin PATB1.
SEQ ID NO:5 sets forth the antisense sequence of CD4B.
SEQ ID NO:6 sets forth the sense sequence of CD4B.
SEQ ID NO:7 sets forth the sequence of EGFP.
SEQ ID NO:8 sets forth the sequence of the GBSS transit peptide.
SEQ ID NO:9 sets forth the sequence of the RuBisCo transit peptide.
SEQ ID NO:10 sets forth the antisense sequence of ADP glucose pyrophosphorylase (AGP).
SEQ ID NO:11 sets forth the sense sequence of ADP glucose pyrophosphorylase (AGP).

DETAILED DESCRIPTION OF THE PREFERRED EMBODIMENTS

In the description and examples that follow, a number of terms are used. In order to provide a clear and consistent understanding of the specification and claims, including the scope to be given such terms, the following definitions are provided. If no definition is provided, all other technical and scientific terms used herein have the same meaning as is commonly understood by one of skill in the art to which the invention belongs.

Coding. As used herein, "coding" or "encoding" refers to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. Contemplated, therefore, are modifications in a DNA sequence which do not substantially affect the functional properties of a protein.

Expression. Denotes the production of a protein product encoded by a gene.

Overexpression. Refers to the production of a gene product in transgenic organisms that exceeds levels of production in normal or non-transgenic organisms.

Percentage of sequence identity. Refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Plant. As used herein, denotes any cellulose-containing plant material that can be genetically manipulated, including but not limited to differentiated or undifferentiated plant cells, protoplasts, whole plants, plant tissues, or plant organs, or any component of a plant such as a leaf, stem, root, bud, tuber, fruit, rhizome, or the like.

Controlling expression. As used here, "controlling expression" denotes controlling the expression of a gene encoding a protein. The effect is either an increase or decrease in the expression level of the sequence compared to its expression level typically observed in a wild-type organism.

Regulating. As used herein, 'regulating' encompasses controlling the expression of a gene encoding a protein. The effect is either an increase or decrease in the expression level of the sequence compared to its expression level typically observed in a wild-type organism.

Expression cassette. As used herein, 'expression cassette' refers to a combination of polynucleotide sequences, comprising one or more regulatory elements and one or more coding sequences. For example, a regulatory element can be a promoter.

Sense suppression of gene expression. As used here, 'sense suppression of gene expression' refers to using a polynucleotide to reduce or eliminate the expression of a target gene. The polynucleotide is designed to express an RNA molecule corresponding to at least a part of a target messenger RNA in the 'sense' orientation. The polynucleotide may correspond to all or part of the coding sequence of the target gene, all or part of the 5' and/or 3' untranslated region of the target gene, or all or part of both the coding sequence and the untranslated regions of the target gene. Typically, a sense suppression element has a substantial sequence identity to the target gene. For example, it can be greater than about 65% sequence identity, greater than about 85% sequence identity, or about 90%, 91%, 92%, 93%, 94%, 95%, 96%, 97%, 98% or 99% sequence identity. The polynucleotide for sense suppression can be at any length so long as it allows for the suppression of the targeted sequence. For example, it may contain 15, 30, 50, 100, 150, 200, 250, 300, 350, 400, 450, 500, 600, 700, 900 nucleotides or longer. See Hamilton et al. *Curr Top Microbiol Immunol.* 197: 77-89 (1995) and U.S. Pat. No. 5,283,184.

Antisense suppression of gene expression. As used herein, an "antisense suppression of gene expression" refers to using a polynucleotide to reduce or eliminate the expression of a target gene. The polynucleotide is designed to express an RNA molecule complementary to all or part of a target messenger RNA. It may correspond to all or part of the complement of the sequence encoding the target gene, all or part of the complement of the 5' and/or 3' untranslated region of the target gene, or all or part of the complement of both the coding sequence and the untranslated regions of the target gene. In addition, the antisense suppression element may be fully complementary (i.e., 100% identical to the complement of the target sequence) or partially complementary (i.e., less than 100% identical to the complement of the target sequence) to the target gene. For example, the polynucleotide may comprise 85%, 90%, 91%, 92%, 93%, 94%, 95%, 96%, 97%, 98%, or 99% sequence complementarity to the target gene. Antisense suppression may be used to inhibit the expression of multiple proteins in the same plant. See, for example, U.S. Pat. No. 5,942,657. Furthermore, the polynucleotide for antisense suppression can be complementary to a portion of the target gene. Generally, sequences of at least 25, 50, 100, 200, 300, 400, 450 nucleotides or greater may be used. Methods for using antisense suppression to inhibit the expression of endogenous genes in plants are described in Liu et al. *Plant Physiol.* 129:1732-1743 (2002) and U.S. Pat. Nos. 5,759,829 and 5,942,657.

RNA suppression of gene expression. As used herein, "RNA suppression of gene expression" refers to using a single-stranded or double-stranded RNA to reduce or eliminate the expression of a target gene. The single-stranded or double-stranded RNA is designed to complement all or part of a target messenger RNA. It may correspond to all or part of the complement of the sequence encoding the target gene, all or part of the complement of the 5' and/or 3' untranslated region of the target gene, or all or part of the complement of both the coding sequence and the untranslated regions of the target gene. The single-stranded or double-stranded RNA can reduce or eliminate the expression level of the target sequence by influencing the level of the target RNA transcript or, alternatively, by influencing translation and thereby affecting the level of the encoded polypeptide. See, for example, U.S. Pat. No. 7,713,735; Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237

Sequence identity. Also referred to as "identity," in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of ordinary skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

Peptide of interest. Peptides are amino acid sequences typically containing 50 or less amino acids. Exemplary and non-limiting peptide includes antimicrobial peptide, peptide epitopes of pathogens, epitope of mite allergen, type II-collagen, amyloid peptides, trastuzumab-binding peptide and tumor associated tandem repeat.

Protein of interest. Protein typically refers to large polypeptides, typically contain more than 50 amino acids. As used herein, protein encompasses any protein of interest. Exemplary and non-limiting proteins include hirudin, insulin, interferon, lactoferrin, hemoglobin, erythropoietin, epidermal growth factor, antibodies, and human and animal vaccines (including attenuated viruses, coat protein and cancer vaccines).

Transgenic plant. Refers to a plant that has incorporated a nucleic acid sequence, including but not limited to genes that are not normally present in a host plant genome, DNA sequences not normally transcribed into RNA or translated into a protein ("expressed"), or any other genes or DNA sequences that one desires to introduce into the non-transformed plant, such as genes that normally may be present in the non-transformed plant but that one desires either to genetically engineer or to have altered expression. The "transgenic plant" category includes both a primary transformant and a plant that includes a transformant in its lineage, e.g., by way of standard introgression or another breeding procedure.

Visual Phenotype. "Visual phenotype" refers to a plant having visually detectable characteristics (for example color change), which can be obtained by expressing a selectible marker gene in a plant. Exemplary selectible marker include chalcone synthase (CHS) gene, anthocyanin synthesis gene, acetohydroxy acid synthase (AHAS) gene, and flavonoid synthesis genes.

Tuber. A thickened, usually underground, food-storing organ that lacks both a basal plate and tunic-like covering, which corms and bulbs have. Roots and shoots grow from growth buds, called "eyes," on the surface of the tuber. Potato tubers are produced by *Solanum tuberosum, S. demis-*

*sum, S. acaule, S. stoloniferum, S. phureja, S. gonicalyx, S. stenotomum, S. berthaultii, S. brevicaule, S. bukasovii, S. canasense, S. gourlayi, S. leptophyes, S. multidissectum, S. oplocense, S. sparsipilum, S. spegazzinii, S. sucrense, S. venturii, S. vernei.*

In one embodiment, peptides and proteins of interest are produced in tetraploid potato plants (for example, *Solanum tuberosum*), which yield greater leaf and tuber biomass and grow faster than diploid potato plants. In another embodiment peptides and protein of interest are produced in a diploid (2n) potato plant that produces small and oddly shaped and colored tubers. Examples include *Solanum chacoense* accessions 414153, 458312, 458314, 472819, 498298, and *Solanum microdontum* accessions 500033, 500035, 500036, 500038, and 558100 that cannot be mistaken for the larger and more uniform tubers from tetraploid (4n) domesticated potato (*Solanum tuberosum*) that are commercially grown for consumption.

Similarly, Applicants have devised methods for producing a protein in a plant in a controlled manner that comprise suppressing at least one endogenous plant protein, such as a potato tuber storage protein, while overexpressing a peptide or protein of interest. For example, and in no way limiting, Applicants have devised an expression cassette to suppress patatin gene expression while overexpressing a peptide or protein of interest. In a different embodiment, Applicants have devised an expression cassette to suppress AGP expression while overexpressing a peptide or protein of interest. To prevent human consumption of such plants and facilitate selection of transgenic plants comprising the protein of interest, an expression cassette may comprise a selectable marker gene conferring a unique color or other unique property upon which selection can be based. Additionally, an inducible promoter may be used to further regulate protein production.

Selectable marker genes include, but are not limited to, GFP, EGFP, GUS, LUX, CAH, SPT, NPTII, HPT, APHIV, BAR, PAT, CHS, AHAS and flavonoid synthesis genes.

In another means for controlling protein expression in a plant, Applicants have devised an expression cassette to suppress protease gene expression while overexpressing a peptide or protein of interest. For example, and in no way limiting, an expression cassette can be used whereby a protease is suppressed and a peptide or protein of interest is produced.

Similarly, in another method for producing a protein in a plant in a controlled manner, Applicants have devised an expression cassette to suppress at least one endogenous plant protein, such as a potato tuber storage protein in addition to suppressing a protease, while overexpressing a therapeutic protein. For example, and in no way limiting, an expression cassette can be used whereby patatin gene expression is suppressed, in addition to a protease such as CD4B, while overexpressing a peptide or protein of interest.

In another method for producing a protein in a plant in a controlled manner, Applicants have devised an expression cassette to suppress the expression of at least one endogenous plant protein, such as a potato starch biosynthetic protein, while overexpressing a therapeutic protein. For example, and in no way limiting, an expression cassette can be used whereby ADP glucose pyrophosphorylase (AGP) expression is suppressed, while overexpressing a peptide or protein of interest.

In yet another method for producing a protein in a plant in a controlled manner, Applicants have devised an expression cassette to suppress the expression of at least one endogenous plant protein, such as a potato starch biosynthetic protein, while overexpressing a protein of interest with a transit peptide. For example, and in no way limiting, an expression cassette can be used whereby ADP glucose pyrophosphorylase (AGP) expression is suppressed, while targeting production of a peptide or protein of interest in a specific site of a transformed potato plant with a transit peptide, such as the RuBisCo transit peptide or the GBSS transit peptide.

Peptides and proteins of interest include, but are not limited to, interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, Rift Valley Fever Virus (RVFV) and HIV vaccine.

All technical terms used herein are terms commonly used in biochemistry, molecular biology and agriculture, and can be understood by one of ordinary skill in the art to which this invention belongs. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997. Methodology involving plant biology techniques is described herein and is described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, e.g., in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage and Caruthers, *Tetra. Letts.* 22:1859-1862 (1981), and Matteucci and Caruthers, *J. Am. Chem. Soc.* 103:3185 (1981).

Restriction enzyme digestions, phosphorylations, ligations and transformations were done as described in Sambrook et al., MOLECULAR CLONING: A LABORATORY MANUAL, $2^{nd}$ ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. Contemplated, therefore, are modifications in a DNA sequence which do not substantially affect the functional properties of a protein.

In this description, "expression" denotes the production of the protein product encoded by a gene. "Overexpression" refers to the production of a gene product in transgenic organisms that exceeds levels of production in normal or non-transgenic organisms.

FURTHER EMBODIMENTS OF THE INVENTION

In addition to the exemplary aspects and embodiments described above, further aspects and embodiments will become apparent by study of the following descriptions.

A. Illustrative Proteins

Any protein can be expressed or suppressed using the present constructs and methodology.

Any protein can be suppressed using a variety of techniques, such as RNAi, antisense, insertional mutagenesis, and other techniques known in the art, according to the methods of the invention. In particular, Applicants have devised methods that comprise the step of suppressing a protease, a storage protein, or a starch biosynthetic protein, while concurrently overexpressing a therapeutic protein of interest. In a non-limiting example, a protease could be suppressed by RNAi, and controlled using an inducible promoter so as not to interfere adversely with the normal growth and development of the plant.

Exemplary protease sequences include but are not limited to the endogenous potato protease sequences disclosed in Table 1:

TABLE 1

Endogenous Potato Proteases

| Potato Protease | GenBank Accession |
| --- | --- |
| *Solanum tuberosum* Asp | AY672651 |
| *Solanum tuberosum* clone 188C11 aspartic protease precursor-like mRNA | DQ241852 |
| *Solanum tuberosum* cathepsin B-like cysteine proteinase | AY450641 |
| *Solanum tuberosum* clone plbr2 cathepsin B-like cysteine proteinase | AY450638 |
| *Solanum tuberosum* clone plbr8 ATP-dependent CLP protease | AY450635 |
| *Solanum tuberosum* mRNA for cysteine protease (cyp gene) | AJ245924 |
| *Solanum tuberosum* subtilisin-like serine protease gene | DQ066722 |
| *Solanum tuberosum* vacuolar processing enzyme 1 (VPE1) | EU605871 |
| *Solanum tuberosum* vacuolar processing enzyme 2 (VPE2) | EU605872 |
| *S. tuberosum* LAP mRNA for leucine aminopeptidase | X67845 |
| *S. tuberosum* LAP mRNA for leucine aminopeptidase | X77015 |
| *S. tuberosum* mRNA for mitochondrial processing peptidase | X66284 |
| *Solanum tuberosum* clone 028E08 mitochondrial processing peptidase-like mRNA | DQ284488 |
| putative aspartic protease A22B (asp1 gene) | AM231414 |

An additional exemplary protease is CD4B, an ATP-dependent protease ATP-binding subunit clpA homolog found in chloroplasts. A Clp protease has chymotrypsin-like activity, and plays a major role in the degradation of misfolded proteins. See Daniell et al., *Theon. Appl. Genet.* 112L 1503-1518 (2006). According to the present invention, silencing of CD4B in potatoes results in higher levels of protein production compared to potatoes that do not have CD4B silenced.

Patatin is a glycoprotein found in *Solanum tuberosum* (sequence as set forth in SEQ ID NO:1). The main function of patatin is as a storage protein. Patatin constitutes up to 40% of the soluble protein in potato tubers, but also exists at much lower levels in other plant organs. See Hofgen et al. *Plant Science,* 66:221-230, (1990).

According to the present invention, silencing of ADP glucose pyrophosphorylase (AGP) in potatoes results in higher levels of protein production compared to potatoes that do not have AGP silenced. AGP produces ADP-glucose, a precursor in the biosynthesis of starch in plants. The constructs of the invention may comprise the full-length AGP sequence or fragments thereof operably linked to two convergent promoters, such that the silencing of AGP is driven by the two promoters from opposite directions. In a particular aspect of the invention, the GBSS promoter drives AGP silencing from one direction and the AGP promoter drives AGP silencing from the opposite direction.

In additional embodiments, protein production according to the invention may be further enhanced by over-expressing a viral suppressor of post-transcriptional gene silencing (PTGS) while suppressing expression of one or more endogenous proteins, such as patatin, CD4B, AGP, or any combination thereof. A preferred viral suppressor of PTGS is the Tobacco blushy stunt virus silencing suppressor P19. PTGS is a nucleotide sequence-specific RNA that prevents gene expression by RNA silencing and thus limits *Agrobacterium*-mediated transformation efficiency in plants. The inventors of the present application have surprisingly discovered that concomitant over-expression of P19 and suppression of one or more potato endogenous proteins dramatically enhance exogenous protein production in potato tubers.

Any protein can be expressed or over-expressed using the silencing constructs of the invention described above. In preferred aspects of the invention, a transit peptide may be used to enhance protein production in a desired site of the transformed plant. Suitable transit peptides include, but are not limited to, the GBSS transit peptide and the RuBisCo transit peptide. For example, and in no way limiting, the constructs of the invention will overexpress a protein or peptide of interest in a potato plant while suppressing expression of one or more endogenous proteins, such as patatin, CD4B, AGP, or any combination thereof.

For example, and in no way limiting, proteins that can be expressed using the instant methodology and constructs are: interleukin-2, hirudin, insulin, interferon, lactoferrin, hemoglobin, erythropoietin, epidermal growth factor, antibodies such as single chain antibodies, and human and animal vaccines (including attenuated viruses, coat protein and cancer vaccines).

Interleukin-2 is a lymphokine produced by normal peripheral blood lymphocytes and induces proliferation of antigen or mitogen stimulated T cells after exposure to antigens or other stimuli. See Morgan et al., *Science* 193:1007-1008 (1976). It was initially called T cell growth factor because of its ability to induce proliferation of stimulated T lymphocytes, it is now recognized that in addition to its growth factor properties it modulates a variety of functions of immune system cells in vitro and in vivo and has been renamed interleukin-2 (IL-2). IL-2 is one of several lymphocyte-produced messenger-regulatory molecules that mediate immunocyte interactions and functions. IL-2 can be produced in plant using the methodology described herein, as demonstrated in the following examples.

Hirudin is a naturally occurring peptide in the salivary glands of medicinal leeches (such as *Hirudo medicinalis*). Hirudin has a blood anticoagulant property, which is essential for leeches' ability to feed on the host's blood because it keeps the blood flowing outside the blood vessels.

Hirudin is the most potent natural inhibitor of thrombin, which converts fibrinogen into fibrin, thereby causing blood coagulation. Because of its anti-coagulation activity, hirudin can be utilized to treat blood coagulation disorders, skin hematomas and superficial varicose veins. However, extracting large amounts of hirudin from natural sources has proved to be difficult. Expression of hirudin through recombinant DNA technology therefore has been developed. Several hirudin based anticoagulant pharmaceutical products are on the market, including Lepirudin, Thrombexx, Revasc and Iprivask (all derived from yeast cells). Comparing with the yeast system, the present technology provides lower costs and more manageable large-scale production.

Insulin is a hormone which regulate carbohydrate and fat metabolism by causing liver, muscle cells and fat tissue to take up glucose from the blood. The glucose are then stored as glycogen in the liver and the muscle. The body keeps insulin at a constant level to remove excess glucose from the blood. Diabetes occur when control of insulin levels fails. External insulin can be used medically to treat some forms of diabetes. The present technology, with the larger-scale and lower-cost production, offers an advantageous approach to produce insulin for medical use.

Interferons are proteins released by host cells in response to the presence of pathogens, such as viruses, bacteria, parasites or tumor cells. In addition to "interfere" with viral replication within host cells, interferons also up-regulate antigen presentation to T lymphocytes and increase the ability of uninfected host cells to resist new infection by virus. The immune effects of interferons have been exploited to treat several diseases, such as actinic keratosis and external genital warts. Additionally, interferon therapy is used (in combination with chemotherapy and radiation) as a treatment for many cancers, including leukemia and lymphomas, such as hairy cell leukemia, chronic myeloid leukemia, nodular lymphoma, cutaneous T-cell lymphoma. Several different types of interferon are approved for use in humans, such as Multiferon™ (known generically as human leukocyte interferon-alpha) and PEGylated interferon-alpha. PEGylation is the process of covalent attachment of polyethylene glycol polymer chains to another molecule, normally a drug or therapeutic protein. The present technology provides a method to produce interferons in large-scale with lower cost.

Lactoferrin, also known as lactotransferrin, is a multifunctional protein of the transferrin family. Lactoferrin belongs to the innate immune system. Apart from its main biological function of binding and transport of iron ions, lactoferrin also has antibacterial, antiviral, antiparasitic, catalytic, anti-cancer, anti-allergic and radioprotecting functions and properties. Lactoferrin prevents bacterial biofilm development. The loss of microbicidal activity and increased formation of biofilm due to decreased lactoferrin activity is observed in cystic fibrosis patients. These findings demonstrate the important role of lactoferrin in human host defense and especially in lung. Lactoferrin with hypothiocyanite has been granted orphan drug status by the FDA. It is therefore highly desirable to be able to produce lactoferrin in large-scale with lower cost. The present technology provides such a production method.

Hemoglobin is the iron-containing oxygen-transport metalloprotein in the red blood cells of all vertebrates. In addition to oxygen, hemoglobin is involved in the transport of other gases: it carries some of the body's respiratory carbon dioxide (about 10% of the total). Hemoglobin also carries the important regulatory molecule nitric oxide bound to a globin protein thiol group, releasing it at the same time as oxygen. The disease of hemoglobin deficiency can be caused either by decreased amount of hemoglobin molecules, as in anemia, or by decreased ability of each molecule to bind oxygen at the same partial pressure of oxygen. Regardless the cause, hemoglobin deficiency decreases blood oxygen-carrying capacity. Supplying the body with external hemoglobin is an important approach to treat hemoglobin deficiency. The present technology provides a method to produce hemoglobin in large-scale with lower cost.

Erythropoietin (also called hematopoietin or hemopoietin) is a glycoprotein hormone that controls erythropoiesis, or red blood cell production. Erythropoietin promotes red blood cell survival through protecting these cells from apoptosis. Erythropoietin also cooperates with various growth factors involved in the development of precursor red cells. Under hypoxic conditions, the kidney will produce and secrete erythropoietin to increase the production of red blood cells. Erythropoietin is also involved in stimulating angiogenesis and inducing proliferation of smooth muscle fibers. Erythropoietin has also been shown to increase iron absorption by suppressing the hormone hepcidin. Medically, erythropoietin has been used to treat anemia resulting from chronic kidney disease, myelodysplasia, and cancer treatment (chemotherapy and radiation). The present technology provides a method to produce erythropoietin in large-scale with lower cost.

Epidermal growth factor (or EGF) is a growth factor that plays an important role in the regulation of cell growth, proliferation, and differentiation by binding to its receptor EGFR. Epidermal growth factor can be found in human platelets, macrophages, urine, saliva, milk, and plasma. Studies have suggested that EGF is important in many physiological processes including spermatogenesis, completion of normal pregnancy, mammary gland development and wound healing. EGF deficiency likely contributes to the pathology of various diseases related with these physiological processes. Comparing with other expression systems, the present technology providing a promising approach to produce EGF in larger scale with lower cost.

Using the present technology, antibodies can be produced recombinantly in plants. For example, and non-limiting, single chain antibodies may be produced in a potato plant.

B. Vaccine and Infection Treatment/Prevention

In addition to the illustrative proteins discussed above, the present technology also provides an advantageous alternative approach to produce human and animal vaccines, including attenuated viruses, coat protein and cancer vaccines. For example, the present technology can be used to produce human vaccines such as anthrax vaccines, cholera vaccine, DPT (diphtheria, pertussis and tetanus) vaccine, hib vaccine, hepatitis A vaccine, hepatitis B vaccine, HPV (Human Papillomavirus) vaccine, influenza vaccine, Japanese Encephalitis vaccine, MMR (measles, mumps and rubella) vaccine, MMRV (measles, mumps, rubella and varicella) vaccine, pneumococcal conjugate vaccine, pneumococcal polysaccharide vaccine, polio vaccine, rotavirus vaccine, smallpox vaccine, tuberculosis vaccine, typhoid vaccine and yellow fever vaccine.

The present technology can be used to produce animal vaccines such as parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine and dewormer vaccine.

The term cancer vaccine refers to a vaccine that either prevents infections with cancer-causing viruses, treats existing cancer or prevents the development of cancer in certain high risk individuals. Some cancers, such as cervical cancer and some liver cancers, are caused by viruses. Traditional vaccines against those viruses, such as HPV (Human Papillomavirus) vaccine and Hepatitis B vaccine, will prevent those cancers.

1. Rift Valley Fever Virus (RVFV)

Additionally, the present technology can be used for treating and/or preventing Rift Valley Fever Virus (RVFV). RVFV is a mosquito-borne-virus whose cyclic epidemics have had devastating economic effects on livestock populations throughout much of sub-Saharan Africa. In humans, RVFV infection causes inflammation of the brain, spinal cord, and meninges, retinitis with visual impairments, and liver necrosis with hemorrhaging. Recent outbreaks have resulted in significant human mortality rates, and an increased geographic footprint, escaping continental Africa into Saudi Arabia and Yemen, demonstrating its capacity to emerge in new regions. Due to its increasing susceptibility, spread, vector plasticity, and ease of aerosolization, RVFV has been listed as an emerging infectious disease and a category A select agent by the Center for Disease Control. Despite being recognized as an emerging threat, relatively little is known about the virulence mechanisms of RVFV and there are currently no FDA licensed vaccines or therapeutics for RVFV. There is an urgent need to develop a greater understanding of viral replication pathways and host cell-related pathogenesis in order to develop novel antiviral therapeutics.

RVFV primarily affects livestock, manifested as fevers and cases of spontaneous abortions in adult animals and high mortality in young animals. In humans, the virus can cause disease with a range of severities. In most cases, the patients develop a mild illness with fever, headache, myalgia and liver abnormalities. In a small percentage of the cases, the illness can progress to hemorrhagic fever or meningoencephalitis. In addition, ocular sequellae can occur that cause retinal damage, including blindness. About 1% of the affected humans die of the disease although, in recent years this percentage has increased (closer to 45%), probably due to increased incidence of people seeking medical attention. An outbreak of RVFV outside endemic countries would cause serious health and agricultural problems. The intentional spread of RVFV is a serious concern of national biosecurity and therefore RVFV is classified as a Category A overlap select agent by the CDC and USDA. Bird et al. *J. Am. Vet Med. Assoc.*, 234(7):883-893 (2009). While Ribavarin is used in some cases as a therapeutic, there are undesirable side effects.

Accordingly, the instant application contemplates methodology and constructs for vaccinating against RVFV. In this regard, and as known in the art, inactivated, live attenuated, and recombinant vaccines can be used for preventing RVFV infection. Likewise, recombinant approaches can be used for producing a protein that inhibits or otherwise alters viral replication and/or transcription. Such proteins can be produced in *planta* using any of the methodology described herein.

2. HIV

Highly active antiretroviral therapy (HAART) has been very successful in managing HIV infections. However, HAART medications do not rid the body of the HIV virus. HIV can remain dormant in the body. Patients can become more symptomatic and more infective if their HAART treatment is interrupted. The Tat protein is produced by HIV and stimulates transcription of the HIV dsRNA. Kim, J. B. and P. A. Sharp, *J. Biol. Chem,* 276 (15):12317-12323 (2001). The Tat protein contains a transduction domain and a nuclear localization signal and therefore this protein can enter cells and the cell's nucleus. Campbell et al., *J. Biol. Chem.,* 279 (46):48197-481204 (2004).

Accordingly, the instant application contemplates methodology and constructs for treating HIV, including impeding HIV infection. For example, and non-limiting, recombinant approaches can be used for producing a protein that inhibits or otherwise alters viral replication and/or transcription. Such proteins can be produced in *planta* using any of the methodology described herein.

3. Hepatitis C Virus

It is estimated that more than 350,000 people worldwide die from HCV-related liver disease every year. Perz et al. *J. Hepatol.* 45:529-538 (2006). HCV is a stealthy killer, often causing its victims no discomfort as it multiplies in their body. The virus manifests itself slowly causing flu-like symptoms such as fever and fatigue and gradually attacks the liver where it causes cirrhosis or cancer. Generally, HCV is transmitted through infected blood. Vaccines are in development.

Accordingly, the instant application contemplates methodology and constructs for treating and/or impeding HCV. In this regard, recombinant approaches can be used for producing a protein that inhibits or otherwise alters viral replication and/or transcription. Such proteins can be produced in *planta* using any of the methodology described herein.

C. Suppression of Gene Expression

A nucleic acid construct can be used to efficiently reduce or prevent the transcription or translation of a target nucleic acid by triggering convergent transcription of a desired polynucleotide encoding, for example, a therapeutic protein. One particular characteristic of such a construct is that, in contrast to conventional silencing constructs, no functional terminator is inserted and operably linked to the 3'-end of a desired polynucleotide.

Another characteristic of an illustrative construct of is that it promotes convergent transcription of one or more copies of polynucleotide that is or are not directly operably linked to a terminator, via two opposing promoters. Due to the absence of a termination signal, the length of the pool of RNA molecules that is transcribed from the first and second promoters may be of various lengths. Occasionally, for instance, the transcriptional machinery may continue to transcribe past the last nucleotide that signifies the "end" of the desired polynucleotide sequence. Accordingly, in this particular arrangement, transcription termination may occur either through the weak and unintended action of downstream sequences that, for instance, promote hairpin formation or through the action of unintended transcriptional terminators located in plant DNA flanking the transfer DNA integration site.

A terminator-free colliding transcription (TFCT) construct, therefore, may comprise a first promoter operably linked to a first polynucleotide and a second promoter operably linked to a second polynucleotide, whereby (1) the first and second polynucleotides share at least some sequence identity with each other and a target sequence, and (2) the first promoter is oriented such that the direction of transcription initiated by this promoter proceeds towards the second promoter, and vice versa, (3) the construct produces RNA molecules that are generally different in size, some transcripts representing the RNA counterparts of at least part of the polynucleotide and others comprising the counterparts of at least some of both the polynucleotide and its inverse complement. See, e.g., U.S. Pat. No. 7,713,735, incorporated by reference in its entirety.

The desired polynucleotide may be linked in two different orientations to the promoter. In one orientation, e.g., "sense," at least the 5'-part of the resultant RNA transcript will share sequence identity with at least part of at least one target transcript. In the other orientation designated as "antisense," at least the 5'-part of the predicted transcript will be identical or homologous to at least part of the inverse complement of at least one target transcript.

A construct may also be characterized in the arrangement of promoters at either side of a desired polynucleotide. Hence, a construct of the present invention may comprise two or more promoters which flank one or more desired polynucleotides or which flank copies of a desired polynucleotide, such that both strands of the desired polynucleotide are transcribed. That is, one promoter may be oriented to initiate transcription of the 5'-end of a desired polynucleotide, while a second promoter may be operably oriented to initiate transcription from the 3'-end of the same desired polynucleotide. The oppositely-oriented promoters may flank multiple copies of the desired polynucleotide. Hence, the "copy number" may vary so that a construct may comprise 2, 3, 4, 5, 6, 7, 8, 9, 10, 15, 20, 30, 40, 50, 60, 70, 80, 90, or 100, or more than 100 copies, or any integer in-between, of a desired polynucleotide ultimately flanked by promoters that are oriented to induce convergent transcription.

Alternatively, a first promoter may be operably linked to a first polynucleotide in "cassette A," for instance, and a second promoter may be operably linked to a second polynucleotide, e.g., "cassette B." The polynucleotides of each cassette may or may not comprise the same nucleotide sequence, but may share some percentage of sequence identity with a target nucleic acid of interest. The cassettes may be tandemly arranged, i.e., so that they are adjacent to one another in the construct. Furthermore, cassette B, for instance, may be oriented in the inverse complementary orientation to cassette A. In this arrangement, therefore, transcription from the promoter of cassette B will proceed in the direction toward the promoter of cassette A. Hence, the cassettes are arranged to induce "convergent transcription."

If neither cassette comprises a terminator sequence, then such a construct, by virtue of the convergent transcription arrangement, may produce RNA transcripts that are of different lengths.

In this situation, therefore, there may exist subpopulations of partially or fully transcribed RNA transcripts that comprise partial or full-length sequences of the transcribed desired polynucleotide from the respective cassette. Alternatively, in the absence of a functional terminator, the transcription machinery may proceed past the end of a desired polynucleotide to produce a transcript that is longer than the length of the desired polynucleotide.

In a construct that comprises two copies of a desired polynucleotide, therefore, where one of the polynucleotides may or may not be oriented in the inverse complementary direction to the other, and where the polynucleotides are operably linked to promoters to induce convergent transcription, and there is no functional terminator in the construct, the transcription machinery that initiates from one desired polynucleotide may proceed to transcribe the other copy of the desired polynucleotide and vice versa. The multiple copies of the desired polynucleotide may be oriented in various permutations: in the case where two copies of the desired polynucleotide are present in the construct, the copies may, for example, both be oriented in same direction, in the reverse orientation to each other, or in the inverse complement orientation to each other, for example.

In an arrangement where one of the desired polynucleotides is oriented in the inverse complementary orientation to the other polynucleotide, an RNA transcript may be produced that comprises not only the "sense" sequence of the first polynucleotide but also the "antisense" sequence from the second polynucleotide. If the first and second polynucleotides comprise the same or substantially the same DNA sequences, then the single RNA transcript may comprise two regions that are complementary to one another and which may, therefore, anneal. Hence, the single RNA transcript that is so transcribed, may form a partial or full hairpin duplex structure.

On the other hand, if two copies of such a long transcript were produced, one from each promoter, then there will exist two RNA molecules, each of which would share regions of sequence complementarity with the other. Hence, the "sense" region of the first RNA transcript may anneal to the "antisense" region of the second RNA transcript and vice versa. In this arrangement, therefore, another RNA duplex may be formed which will consist of two separate RNA transcripts, as opposed to a hairpin duplex that forms from a single self-complementary RNA transcript.

Alternatively, two copies of the desired polynucleotide may be oriented in the same direction so that, in the case of transcription read-through, the long RNA transcript that is produced from one promoter may comprise, for instance, the sense sequence of the first copy of the desired polynucleotide and also the sense sequence of the second copy of the desired polynucleotide. The RNA transcript that is produced from the other convergently-oriented promoter, therefore, may comprise the antisense sequence of the second copy of the desired polynucleotide and also the antisense sequence of the first polynucleotide. Accordingly, it is likely that neither RNA transcript would contain regions of exact complementarity and, therefore, neither RNA transcript is likely to fold on itself to produce a hairpin structure. On the other hand the two individual RNA transcripts could hybridize and anneal to one another to form an RNA duplex.

Hence, in one aspect, the present invention provides a construct that lacks a terminator or lacks a terminator that is preceded by self-splicing ribozyme encoding DNA region, but which comprises a first promoter that is operably linked to a first polynucleotide and a second promoter that is operably linked to second polynucleotide, whereby (1) the first and second polynucleotide share at least some sequence identity with each other, (2) the first promoter is oriented such that the direction of transcription initiated by this promoter proceeds towards the second promoter, and vice versa, and (3) this convergent arrangement produces a range of RNA transcripts that are generally different in length.

The desired polynucleotides may be perfect or imperfect repeats of one another, or perfect or imperfect inverse complementary repeats of one another. In the case of a construct that comprises a first polynucleotide and a second polynucleotide, the second polynucleotide may be fully or partially identical in nucleotide sequence to the first polynucleotide and oriented in the direct or inverse complementary orientation with respect to the first polynucleotide. Hence, the first and second polynucleotides may be perfect repeats of one another. On the other hand, the second polynucleotide may be an imperfect repeat of the first polynucleotide, that is the second polynucleotide may share sequence identity with the first polynucleotide, but is not fully or partially identical in sequence, i.e., the second polynucleotide is an imperfect repeat. That second polynucleotide also may be oriented as a direct repeat or positioned in the inverse complementary orientation with respect to the first polynucleotide.

Any of the polynucleotides described herein, such as a desired polynucleotide, or a first or second polynucleotide, for instance, may be identical to at least a part of a target sequence, or may share sequence identity with at least a part of a target sequence. When a desired polynucleotide comprises a sequence that is homologous to a fragment of a target sequence, i.e., it shares sequence identity with "at least a part of" a target sequence, then it may be desirable that the nucleotide sequence of the fragment is specific to the target gene, and/or the partial perfect or imperfect sequence of the target that is present in the desired polynucleotide is of sufficient length to confer target-specificity. Hence the portion of the desired polynucleotide that shares sequence identity with a part of a target sequence may comprise a characteristic domain, binding site, or nucleotide sequence typically conserved by isoforms or homologs of the target sequence. It is possible, therefore, to design a desired polynucleotide that is optimal for targeting a target nucleic acid in a cell.

In another embodiment, the desired polynucleotide comprises a sequence of preferably between 4 and 5,000 nucleotides, more preferably between 50 and 1,000 nucleotides, and most preferably between 150 and 500 nucleotides that share sequence identity with the DNA or RNA sequence of a target nucleic acid. The desired polynucleotide may share sequence identity with at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 300, 400, 500, or more than 500 contiguous nucleotides, or any integer in between, that are 100% identical in sequence with a sequence in a target sequence, or a desired polynucleotide comprises a sequence that shares about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%. 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 8%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% nucleotide sequence identity with a sequence of the target sequence. In other words the desired polynucleotide may be homologous to or share homology with the full-length sequence of a target sequence or a fragment thereof of a target sequence.

Hence, the present invention provides an isolated nucleic acid molecule comprising a polynucleotide that shares homology with a target sequence and which, therefore, may hybridize under stringent or moderate hybridization conditions to a portion of a target sequence described herein. By a polynucleotide which hybridizes to a "portion" of a polynucleotide is intended a polynucleotide (either DNA or RNA) hybridizing to at least about 15 nucleotides, and more preferably at least about 20 nucleotides, and still more preferably at least about 30 nucleotides, and even more preferably more than 30 nucleotides of the reference polynucleotide. For the purpose of the invention, two sequences that share homology, i.e., a desired polynucleotide and a target sequence, may hybridize when they form a double-stranded complex in a hybridization solution of 6.times.SSC, 0.5% SDS, 5× Denhardt's solution and 100 g of non-specific carrier DNA. See Ausubel et al., section 2.9, supplement 27 (1994). Such sequence may hybridize at "moderate stringency," which is defined as a temperature of 60° C. in a hybridization solution of 6.times.SSC, 0.5% SDS, 5× Denhardt's solution and 100 µug of non-specific carrier DNA. For "high stringency" hybridization, the temperature is increased to 68° C. Following the moderate stringency hybridization reaction, the nucleotides are washed in a solution of 2.times.SSC plus 0.05% SDS 5× at room temperature, with subsequent washes with 0.1.times.SSC plus 0.1% SDS at 60° C. for 1 h. For high stringency, the wash temperature is increased to typically a temperature that is about 68° C. Hybridized nucleotides may be those that are detected using 1 ng of a radiolabeled probe having a specific radioactivity of 10,000 cpm/ng, where the hybridized nucleotides are clearly visible following exposure to X-ray film at −70° C. for no more than 72 hours.

In one embodiment, a construct of the present invention may comprise an expression cassette that produces a nucleic acid that reduces the expression level of a target gene that is normally expressed by a cell containing the construct, by 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% in comparison to a cell that does not contain the construct.

Any polynucleotide of the present invention, be it a "desired polynucleotide," a "first" polynucleotide, a "second" polynucleotide may share a certain percentage sequence identity with a target sequence. As explained herein, a target sequence may be, but is not limited to, a sequence, partial or full-length, of a gene, regulatory element, such as a promoter or terminator, exon, intron, an untranslated region, or any sequence upstream or downstream of a target genomic sequence. Accordingly, a polynucleotide of the present invention, may comprise a sequence that is identical over the length of that sequence to such a target sequence. On the other hand, the polynucleotide of the present invention, may comprise a sequence that shares sequence identity to such a target sequence. Hence, a desired polynucleotide of the present invention may share about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% nucleotide sequence identity with a sequence of the target sequence.

As used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity)

and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of ordinary skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215:403-410 (1990); and, Altschul et al., Nucleic Acids Res. 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters can be employed alone or in combination.

Multiple alignment of the sequences can be performed using the CLUSTAL method of alignment (Higgins and Sharp (1989) CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

Thus, and in no way limiting, Applicants contemplate suppressing an endogenous plant gene encoding a protein, while concurrently overexpressing a gene encoding a protein of interest. For example, a convergent expression cassette can be used that concurrently suppresses patatin (major tubor storage protein), yet overexpresses a therapeutic protein of interest. Such expression cassette may comprise a selectable marker gene conferring a unique color or other unique property upon which selection can be based, thereby facilitating selection and preventing human consumption.

Additionally, an inducible promoter may be used to further regulate protein suppression and/or production, such that protein suppression and/or production does not interfere with the normal growth and development of the plant.

D. Regulatory Elements in Nucleic Acid Construct

The present disclosure provides nucleic acid molecules and methodology for regulating protein production in a transgenic plant. In one embodiment, and as discussed above, a therapeutic protein of interest can be overexpressed in a potato plant.

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.,* 86:1216 (1988); Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986)). Other selectable marker genes confer resistance to herbicides such as glyphosate, glufosinate, or bromoxynil (Comai, et al., *Nature,* 317:741-744 (1985); Gordon-Kamm, et al., *Plant Cell,* 2:603-618 (1990); Stalker, et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci. USA,* 84:131 (1987); DeBlock, et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science,* 263:802 (1994)). GFP and mutants of GFP may be used as screenable markers. One example of a GFP mutant is enhanced green fluorescent protein (EGFP), which has increased fluorescence and photostability.

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See, Ward, et al., *Plant Mol. Biol.,* 22:361-366 (1993). Exemplary inducible promoters include, but are not limited to, that from the ACEI system which responds to copper (Mett, et al., *Proc. Natl. Acad. Sci. USA,* 90:4567-4571 (1993)); In2 gene from maize which responds to benzenesulfonamide herbicide safeners (Hershey, et al., *Mol. Gen Genetics,* 227:229-237 (1991); Gatz, et al., *Mol. Gen. Genetics,* 243:32-38 (1994)); or Tet repressor from Tn10 (Gatz, et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena, et al., *Proc. Natl. Acad. Sci. USA*, 88:10421-10425 (1991)).

Other promoters can be cloned from bacterial species such as the promoters of the nopaline synthase and octopine synthase gene. There are various inducible promoters, but typically an inducible promoter can be a temperature-sensitive promoter, a chemically-induced promoter, or a temporal promoter. Specifically, an inducible promoter can be induced by any of, for example, ethanol, sterol, sugar, ethylene, ABA, auxin, cytokinin, octopine, nopaline, light, oxygen, cadmium, copper, and other heavy metals. Exemplary inducible promoters also include but are not limited to Ha hsp 17.7 G4 promoter, a wheat wcs120 promoter, a Rab 16A gene promoter, an alpha.-amylase gene promoter, a pin2 gene promoter, and a carboxylase promoter.

Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989); Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)); and maize H3 histone (Lepetit, et al., *Mol. Gen. Genetics*, 231:276-285 (1992); Atanassova, et al., *Plant Journal*, 2 (3):291-300 (1992)). The ALS promoter, an XbaI/NcoI fragment 5' to the *Brassica napus* ALS3 structural gene (or a nucleotide sequence similarity to said XbaI/NcoI fragment), represents a particularly useful constitutive promoter. See PCT Application WO 96/30530. Additional constitutive promoters include cauliflower mosaic virus promoters, figwort mosaic virus promoters, and plant promoters of a rubisco activase gene.

Tissue-Specific or Tissue-Preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., *Science*, 23:476-482 (1983); Sengupta-Gopalan, et al., *Proc. Natl. Acad. Sci. USA*, 82:3320-3324 (1985)); a leaf-specific and light-induced promoter such as that from cab or rubisco (Simpson, et al., *EMBO J.*, 4(11): 2723-2729 (1985); Timko, et al., *Nature*, 318:579-582 (1985)); an anther-specific promoter such as that from LAT52 (Twell, et al., *Mol. Gen. Genetics*, 217:240-245 (1989)); a pollen-specific promoter such as that from Zm13 (Guerrero, et al., *Mol. Gen. Genetics*, 244:161-168 (1993)); or a microspore-preferred promoter such as that from apg (Twell, et al., *Sex. Plant Reprod.*, 6:217-224 (1993)).

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. One example of such sequence is a transit peptide coding sequence in granule-bound starch synthase (GBSS) gene. Another example is a sequence derived from the small subunit of the ribulose 1,5-diphosphate carboxylase oxygenase (RuBisCo) gene. For other examples, see Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant J.*, 2:129 (1991); Kalderon, et al., *Cell*, 39:499-509 (1984); Steifel, et al., *Plant Cell*, 2:785-793 (1990).

Depending on the specific application, an appropriate promoter sequence can be used. For example, the promoters may be constitutive or inducible promoters or permutations thereof "Strong" promoters, for instance, can be those isolated from viruses, such as cauliflower mosaic virus, rice tungro bacilliform virus, maize streak virus, cassava vein virus, mirabilis virus, peanut chlorotic streak caulimovirus, figwort mosaic virus and chlorella virus. In one embodiment, and as known in the art, Applicants contemplates the constitutive 35S promoter from cauliflower mosaic virus.

E. Potato Plants for Genetic Engineering

In the present description, "transgenic plant" refers to a plant that has incorporated a nucleic acid sequence, including but not limited to genes that are not normally present in a host plant genome, DNA sequences not normally transcribed into RNA or translated into a protein ("expressed"), or any other genes or DNA sequences that one desires to introduce into the non-transformed plant, such as genes that normally may be present in the non-transformed plant but that one desires either to genetically engineer or to have altered expression. The "transgenic plant" category includes both a primary transformant and a plant that includes a transformant in its lineage, e.g., by way of standard introgression or another breeding procedure.

Peptides and proteins of interest can be produced both in diploid and tetraploid potato plants (for example, *Solanum tuberosum*). The terms "diploid" and "tetraploid" as used herein are defined as having two and four pairs of each chromosome in each cell (excluding reproductive cells). Diploid potato plant produced small and oddly shaped and colored tubers. Tetraploid potato plants yield greater leaf and tuber biomass and grow faster than diploid potato plants. Tetraploid potato plants are commercially grown for consumption.

F. Methodology for Genetic Engineering

A nucleic acid construct can be introduced into any plant cell using a suitable genetic engineering technique. Both monocotyledonous and dicotyledonous angiosperm or gymnosperm plant cells may be genetically engineered in various ways known to the art. For example, see Klein et al., *Biotechnology* 4:583-590 (1993); Bechtold et al., *C. R. Acad. Sci. Paris* 316:1194-1199 (1993); Bent et al., *Mol. Gen. Genet.* 204:383-396 (1986); Paszowski et al., *EMBO J.* 3:2717-2722 (1984); Sagi et al., *Plant Cell Rep.* 13:262-266

(1994). Exemplary methodology include but are not limited to transformation, electroporation, particle gun bombardment, calcium phosphate precipitation, and polyethylene glycol fusion, transfer into germinating pollen grains, direct transformation (Lorz et al., *Mol. Genet.* 199:179-182 (1985)), and other methods known to the art.

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

*Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki et al., supra, and Moloney, et al., *Plant Cell Reports*, 8:238 (1989). See also, U.S. Pat. No. 5,563,055 (Townsend and Thomas), issued Oct. 8, 1996.

In one embodiment, an *Agrobacterium* species such as *A. tumefaciens* and *A. rhizogenes* can be used, for example, in accordance with Nagel et al., *Microbiol Lett* 67:325 (1990). Briefly, *Agrobacterium* may be transformed with a plant expression vector via, e.g., electroporation, after which the *Agrobacterium* is introduced to plant cells via, e.g., the well known leaf-disk method.

The *Agrobacterium* transformation methods discussed above are known to be useful for transforming dicots. Additionally, de la Pena, et al., *Nature* 325:274-276 (1987), Rhodes, et al., *Science* 240:204-207 (1988), and Shimamato, et al., *Nature* 328:274-276 (1989), all of which are incorporated by reference, have transformed cereal monocots using *Agrobacterium*. Also see Bechtold, et al., *C.R. Acad. Sci. Paris* 316 (1994), showing the use of vacuum infiltration for *Agrobacterium*-mediated transformation.

In one embodiment, a transformation vector may comprise an alternative to the *Agrobacterium*-derived T-DNA element, which is characterized by a "left border" at its 5'-end, and a "right border" at its 3'-end. Accordingly, the alternative transfer DNA may be isolated from an edible plant in order to minimize the quantity of undesirable nucleic acids introduced into the target plant genome. Such a plant transfer DNA (P-DNA) also is delineated by left and right border-like sequences that support the transfer of one polynucleotide into another. For present purposes, either T-DNA or P-DNA constructs can be used to transfer a desired polynucleotide into a plant cell. The skilled artisan would understand that, in some instances, it is desirable to reduce the amount and number of undesirable genetic elements that are introduced into a plant genome via *Agrobacterium*-mediated transformation. Accordingly, the skilled artisan could use the P-DNA in such instances, because the P-DNA, and its border-like sequences, is isolated from a plant genome. See, e.g., U.S. Pat. Nos. 7,598,430 and 7,928,292.

Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described (Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994)).

The exact plant transformation methodology may vary somewhat depending on the plant species and the plant cell type (e.g. seedling derived cell types such as hypocotyls and cotyledons or embryonic tissue) that is selected as the cell target for transformation. Plant species specific transformation protocols may be found in: Biotechnology in Agriculture and Forestry 46: Transgenic Crops I (Y. P. S. Bajaj ed.), Springer-Verlag, New York (1999), and Biotechnology in Agriculture and Forestry 47: Transgenic Crops II (Y. P. S. Bajaj ed.), Springer-Verlag, New York (2001).

Following transformation, the plant cells are grown and upon the emergence of differentiating tissue, such as shoots and roots, mature plants are regenerated. Typically a plurality of plants is regenerated. Methodologies to regenerate plants are generally plant species and cell type dependent and are known to those skilled in the art. Further guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

To assist in selection of genetically engineered plant material, a selectable/screenable marker makes it possible to distinguish from other plants or plant tissues that do not express a heterologous gene. Screening procedures may require assays for expression of proteins encoded by the screenable marker gene. Examples of such markers include the beta glucuronidase (GUS) gene, green fluorescent protein (GFP), and the luciferase (LUX) gene. Likewise, a gene encoding resistance to a fertilizer, antibiotic, herbicide or toxic compound can be used to identify transformation events. Examples of selectable markers include the cyanamide hydratase gene (CAH) streptomycin phosphotransferase (SPT) gene encoding streptomycin resistance, the neomycin phosphotransferase (NPTII) gene encoding kanamycin and geneticin resistance, the hygromycin phosphotransferase (HPT or APHIV) gene encoding resistance to hygromycin, acetolactate synthase (a/s) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

A transgenic plant can be crossed or self-fertilized to transmit the desired gene or nucleotide sequence to progeny plants. Seedlings of this next generation of transgenic plants can be screened for the presence of a desired polynucleotide using standard techniques such as PCR, enzyme or phenotypic assays, ELISA, or Western blot analysis. Alternatively, if the transformation vector comprises a selectable/screenable marker(s), the plant progeny may be selected for resistance or tolerance to a particular substance, or expression of a unique phenotype such as a color, hair, or other unique trait.

G. Cultivating Plants in a Greenhouse for Continuous Production of a Target Protein in Plants The method of instant invention can circumvent the limitations imposed by natural crop growth cycles. By producing the transgenic plant under defined environmental conditions using controlled environment agriculture in a greenhouse, the transgenic plant can be cultivated at any time of the year under conditions that optimize production of plant biomass. As a consequence, the method of the instant invention provides a continuous supply of the protein of interest without the seasonal disruptions associated with an open field agriculture system. Once the transgenic plant containing the protein of interest is harvested, these plants are immediately replaced with new transgenic plants so that the invention can be practiced on a continuous basis. This system allows for efficient and continuous processing of plant biomass thereby increasing the annual protein productivity rate and minimizing equipment size and capital costs associated with downstream processing.

H. Protein Isolation, Purification and Quantification

Depending on the type protein produced and the location of the protein, other protein extraction protocols are also known and readily available to an ordinarily skilled artisan. For example and in no way limiting the protein produced could be located in the leaves, stem or tuber of the plant. Likewise, and again depending upon the intended use of the therapeutic protein, various purification protocols and reagents are known and readily available.

The extraction, isolation and purification of plant derived proteins from potato tubers are well known in the art. See, for example, Maelville et al., *J. Bio. Chem.* 247:3445-3453 (1972) and Bryant et al., *Biochem.* 15:3418-3424, (1976). Typically, potatoes are sliced with peels intact and homogenized and expressed through a filter. The resulting juice is pH adjusted, centrifuged, and fractionated. Purification is achieved through water washing and heat treatment whereby clear filtrated fractions are pooled and lyophilized. Crude extract is obtained by suspending the lyophilized powder in water, dialyzing it against water, and lyophilizing the resulting clear filtrate. The crude extract can be analyzed by various technics such as HPLC and Mass Spectrometry.

The extraction, isolation and purification of proteins from leaves are also described in the literature. See, for example, U.S. Pat. Nos. 4,400,471 and 4,268,632. The succulent leaves of plants, such as tobacco, spinach, soybean, and alfalfa, are typically composed of 10-20% solids, the remaining fraction being water. The solid portion is composed of a water soluble and a water insoluble portion, the latter being predominantly composed of the fibrous structural material of the leaf. The water soluble portion includes compounds of relatively low molecular weight (MW), such as sugars, vitamins, alkaloids, flavors, amino acids, and other compounds of relatively high MW, such as natural and recombinant proteins. Proteins in the soluble portion of the plant tissue can be further divided into two fractions. One fraction comprises predominantly a photosynthetic enzyme, Rubisco. The Rubisco enzyme has a molecular weight of about 550 kD. This fraction is commonly referred to as "fraction 1 protein." Rubisco is abundant, comprising up to 25% of the total protein content of a leaf and up to 10% of the solid matter of a leaf. The other fraction contains a mixture of proteins and peptides have molecular weights typically ranging from about 3 kD to about 100 kD and other compounds including sugars, vitamins, alkaloids and amino acids. This fraction is collectively referred to as "fraction 2 proteins." Fraction 2 proteins can be native host materials, heterologous proteins and peptides. Transgenic plants may also contain plant virus particles having a molecular size greater than 1,000 kD.

The basic process for isolating plant proteins generally begins with disintegrating leaf tissue and pressing the resulting pulp to produce a raw plant extract. The process is typically performed in the presence of a reducing agent or antioxidant to suppress undesirable oxidation. The raw plant extract, which contains various protein components and finely particulate green pigmented material, is pH adjusted and heated. The typical pH range for the raw plant extract after adjustment is between about 5.3 and about 6.0. This range has been optimized for the isolation of fraction 1 protein. Heating, which causes the coagulation of green-pigmented material, is typically controlled near 50° C. The coagulated green-pigmented material can then be removed by moderate centrifugation to yield a secondary plant extract. The secondary plant extract is subsequently cooled and stored at a temperature at or below room temperature. After an extended period of time, e.g. 24 hours, Rubisco is crystallized from the brown juice. The crystallized fraction 1 protein can subsequently be separated from the liquid by centrifugation. Fraction 2 proteins remain in the liquid, and they can be purified upon further acidification to a pH near 4.5. Alternatively, the crystal formation of Rubisco from secondary plant extract can be induced by adding sufficient quantities of polyethylene glycol (PEG) in lieu of cooling. The crystallized fraction protein can be dissolved in certain buffers for other analysis.

The instant transgenic plants are characterized by increased production of a therapeutic protein, compared with a wild-type control plant. A quantitative increase of a protein can be assayed by several methods known in the art, including but not limited to Western blot analysis, ELISA, as well as a standard Bradford assay.

Pharmaceutical formulations may be prepared from the purified protein and such formulations may be used to treat suitable diseases or conditions. Generally and as known in the art, the purified protein will be admixed with a pharmaceutically acceptable carrier or diluent in amounts sufficient to exert a therapeutically useful effect in the absence of undesirable side effects on the patient treated. To formulate such a composition, the weight fraction of the protein is dissolved, suspended, dispersed or otherwise mixed in a selected carrier or diluent at an effective concentration such that the treated condition is ameliorated. It is understood however that concentrations and dosages may vary in accordance with the severity of the condition alleviated. It is further understood that for any particular subject, specific dosage regimens may be adjusted over time according to individual judgment of the person administering or supervising administration of the formulations.

Pharmaceutical solutions or suspensions may include for example a sterile diluent such as, for example, water, lactose, sucrose, dicalcium phosphate, or carboxymethyl cellulose. Carriers that may be used include water, saline solution, aqueous dextrose, glycerol, glycols, ethanol and the like, to thereby form a solution or suspension. If desired the pharmaceutical compositions may also contain non-toxic auxiliary substances such a wetting agents; emulsifying agents; solubilizing agents; antimicrobial agents, such as benzyl alcohol and methyl parabens; antioxidants, such as ascorbic acid and sodium bisulfite; chelating agents such as ethylenediaminetetraacetic acid (EDTA); pH buffering agents such as actetate, citrate or phosphate buffers; and combinations thereof.

I. Edible Vaccine Production in Transgenic Potatoes

Vaccine proteins expressed in plants may provide an "edible vaccine," whereby ingestion of plants containing the vaccine by a human would stimulate an increased immune response and provide immunization against the virus. See, for example, Mason et al., Proc. Natl. Acad. Sci. USA, 89:11745-11749 (1992). The high cost of production and purification of synthetic peptides manufactured by chemical or fermentation based processes may prevent their broad scale use as oral vaccines. The production of immunogenic proteins in transgenic plants, on the other hand, offers an economical alternative. Attempts have been made to produce transgenic plants that express bacterial antigens of E. coli and Streptococcus mutants. For instance, Curtiss et al. (WO90/0248) report the transformation of sunflower with the E. coli LT-B gene. Also, the expression of LT-B and its assembly into G.sub.M1-binding pentamers in tobacco and potato plants has been reported (Haq et al. 1995). Additionally, Arntzen et al. (WO96/12801) disclose vectors for the independent and coordinate expression of LT-A and LT-B, which optionally contain a SEKDEL (SEQ ID NO: 12) microsomal rentention signal.

Edible vaccines are produced by transforming a transgenic plant with a vector containing a vaccine gene. The production of vaccine can be detected by Western blot analysis, ELISA, as well as a standard Bradford assay. The vaccine producing transgenic plant can be administered without processing.

Alternatively, the transgenic plant may be processed by lyophilizing or dehydrating the plant material to remove water. "Dehydration" may be performed by air drying or spray drying or by "lyophilization," wherein the "lyophilization" refers to the preparation of a plant composition in dry form by rapid freezing and dehydration in the frozen state (sometimes referred to as sublimation). This process may take place under vacuum at a pressure sufficient to maintain frozen product with the ambient temperature of the containing vessel at about room temperature, preferably less than about 500 mTorr, more preferably less than about 200 mTorr, even more preferably less than about 1 mTorr, for between about 1 hour to 72 hours. Plant material may be "dehydrated" by placing the plant material in an oven with a temperature between about 60° C. and 200° C. for between about 1 hour to 72 hours. Plant material is deemed to be sufficiently "lyophilized" or "dehydrated" when the weight of the plant material ceases to change over time. For example, the weight of plant material placed in an oven at temperatures described above will decrease over time as water evaporates. When the weight ceases to change, all of the water has evaporated, and the plant material can be said to be "dehydrated." Preferably, by whatever drying method is used, the final material is dehydrated sufficiently to remove at least 90% of all the water content by weight. The "lyophilized" or "dehydrated" plant material may be further "processed" by emulsifying the "lyophilized" or "dehydrated" plant material with excipients which are pharmaceutically acceptable and compatible with the contraceptive polypeptide. Suitable excipients include, for example, water, saline, dextrose, glycerol, ethanol, or the like and combinations thereof, wherein the "lyophilized" or "dehydrated" plant material comprises at least 40% and preferably at least 50% by weight of the excipient mixture. In addition, if desired, the "lyophilized" or "dehydrated" plant material may contain minor amounts of auxiliary substances such as wetting or emulsifying agents, pH buffering agents, or adjuvants which enhance the effectiveness of the plant material. As used herein, "lyophilized" or "dehydrated" plant material may be further processed by admixing the plant material with a pharmaceutically acceptable creams, ointments, salves, or suppositories, wherein the plant material comprises at least 40% and preferably at least 50% by weight of the admixture. Alternatively, "dehydrated" plant material may be further processed by reconstituting the plant material with a liquid, such as, but not limited to, fruit juice, vegetable juice, milk, water, or other vaccine formulations to form multivalent or multicomponent vaccines.

The following examples are given to illustrate the present invention. It should be understood, however, that the invention is not to be limited to the specific conditions or details described in these examples. Throughout the specification, any and all references to publicly available documents are specifically incorporated by reference.

EXAMPLES

Specific examples are presented below of methods and constructs. They are meant to be exemplary and not as limitations on the present invention.

Example 1

Targeted Expression of GFP

Figure 20:
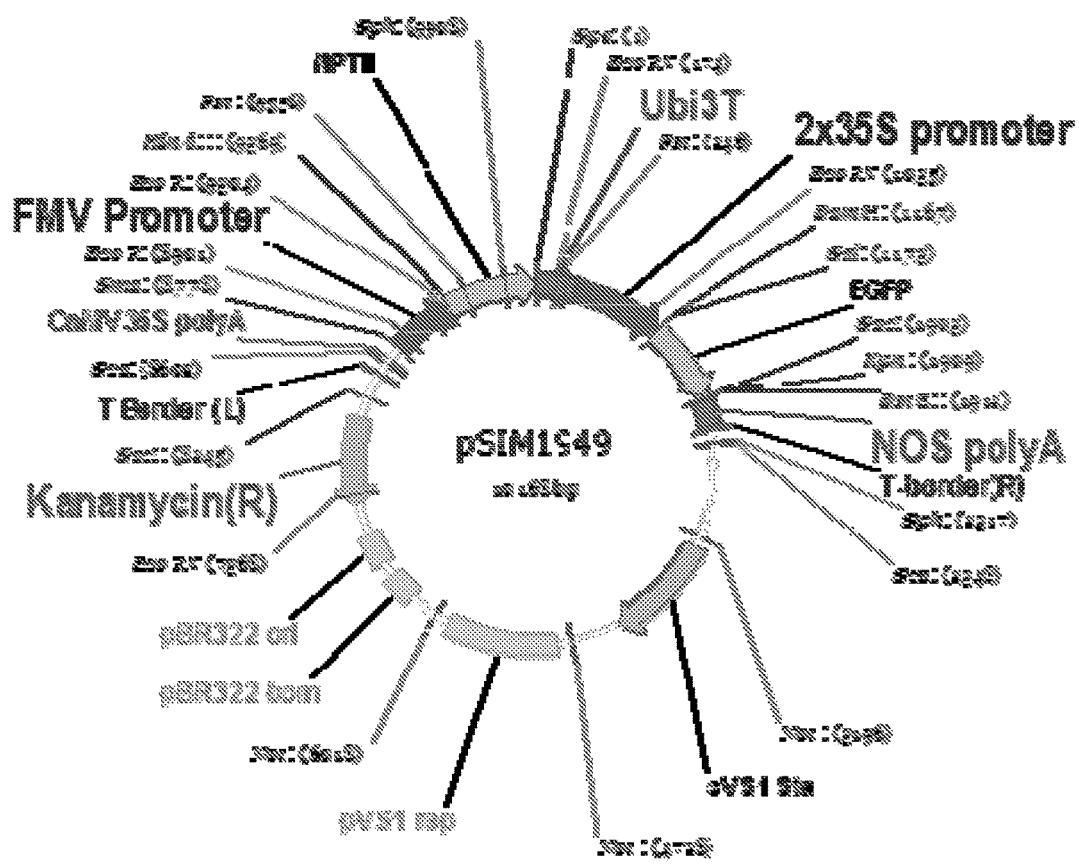
FIG. 20. Map of the pSIM1949-2×35S::EGFP gene control vector.
Figure 21:
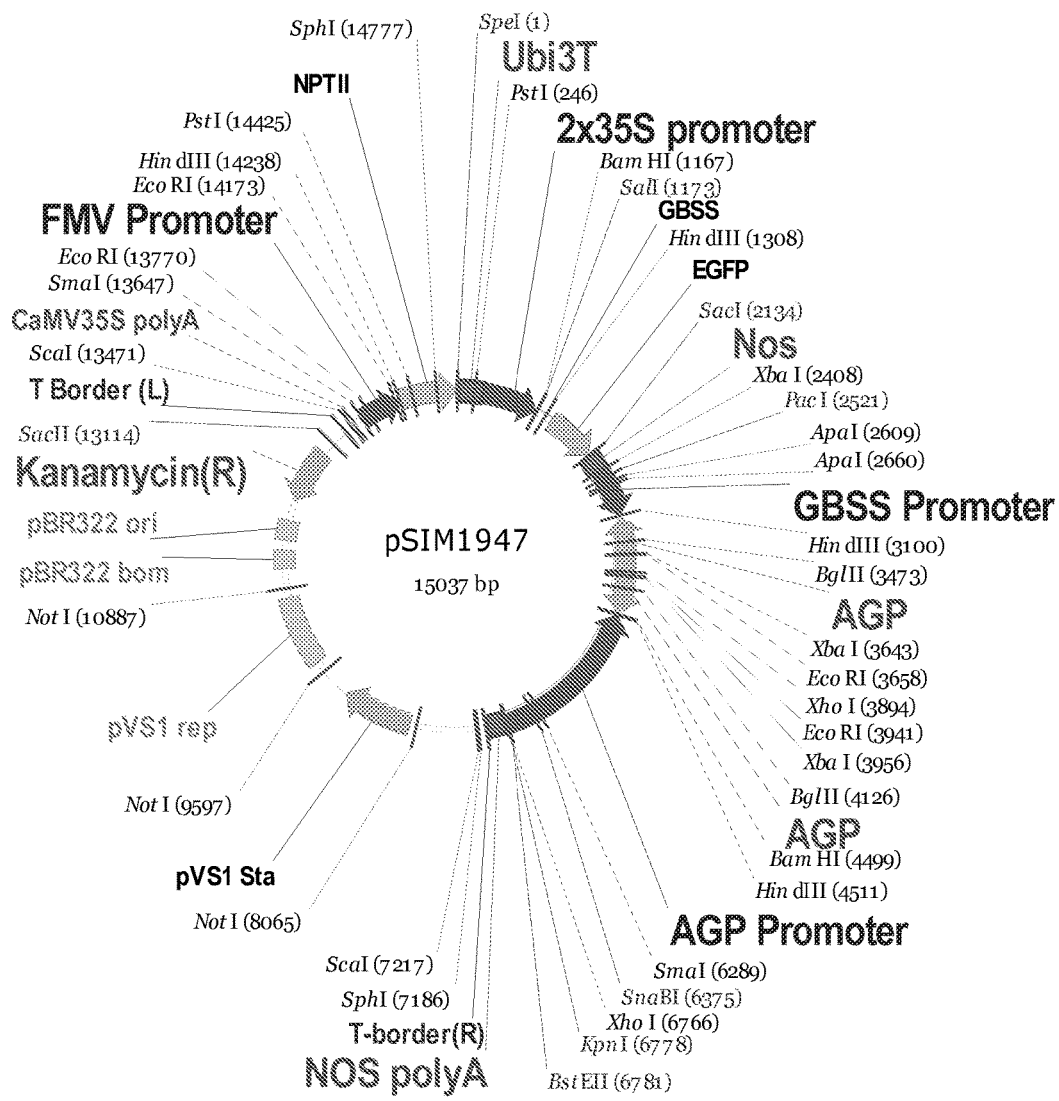
FIG. 21. Map of the vector pSIM1947. pSIM1947 carries the 2×35S::GBSS$^{TP}$-eGFP cassette and the GBSS->sAGP<-AGP cassette. GFP expression is driven by the GBSS transit peptide and AGP silencing is driven by the GBSS promoter from one direction and by the AGP promoter from the opposite direction.
Figure 22:
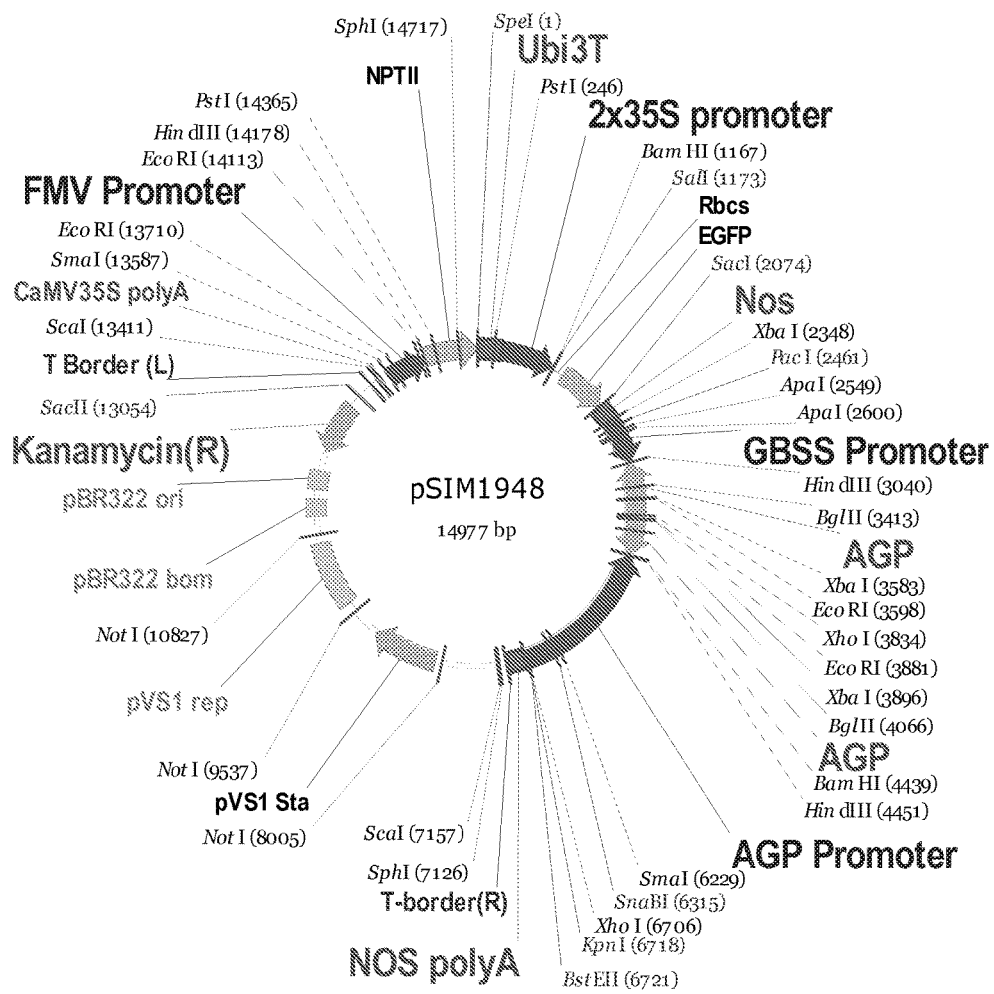
FIG. 22. Map of the vector pSIM1948. pSIM1948 carries the 2×355: Rbcs$^{TP}$-eGFP cassette and the GBSS->sAGP<-AGP cassette. GFP expression is driven by the RuBisCo transit peptide and AGP silencing is driven by the GBSS promoter from one direction and by the AGP promoter from the opposite direction.
Figure 23:
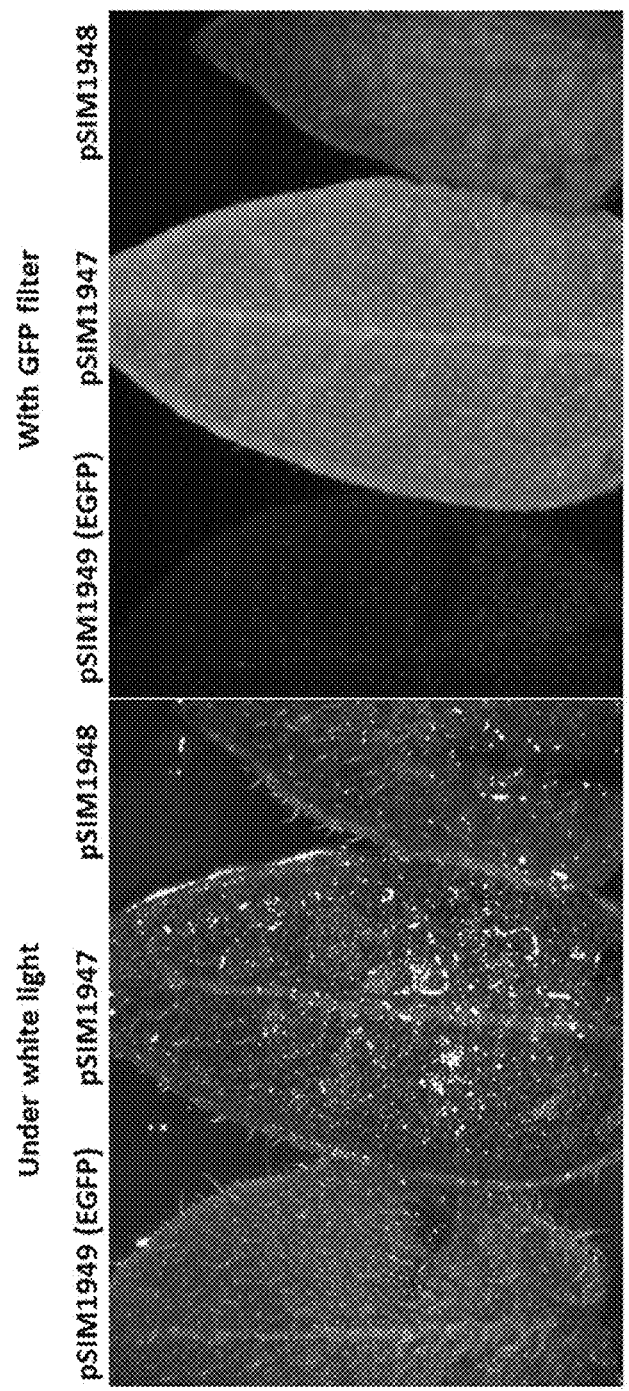
FIG. 23. GFP expression in young potato leaves. Potato plants were transformed with pSIM1947 (FIG. 21) or pSIM1948 (FIG. 22). Transgenic shoots growing in vitro strongly expressing GFP were selected using fluorescence microscopy and GFP expression was evaluated as compared to control lines transformed with the control vector pSIM1949 (FIG. 20). The left panel shows leaves under white light and the right panel shows leaves with a GFP filter. Strong GFP expression was detected in the leaves of transgenic pSIM1947 plantlets. GFP expression in pSIM1948 plantlets was only slightly stronger than GFP expression in the control lines. These results indicate that concomitant protein over-expression with the GBSS transit peptide and AGP silencing by convergent promoters are effective in enhancing recombinant protein production.
Figure 24:
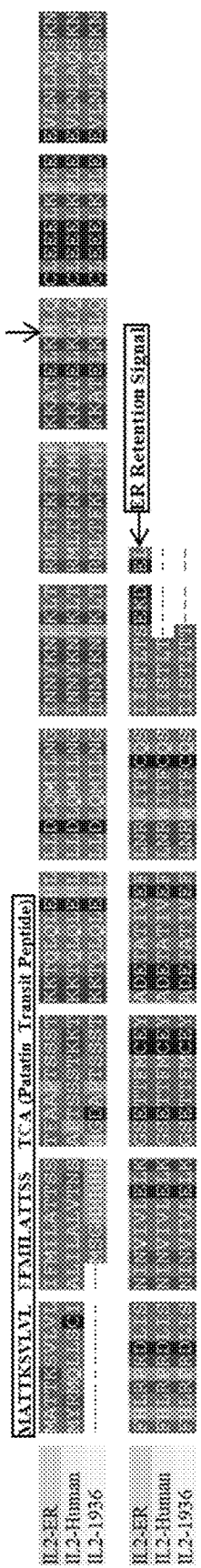
FIG. 24. Truncated version of the human interleukin 2 (IL-2) placed between a *Solanum tuberosum* patatin ER transit peptide (N-terminus) and an ER retention signal (C-terminus).
Figure 25:
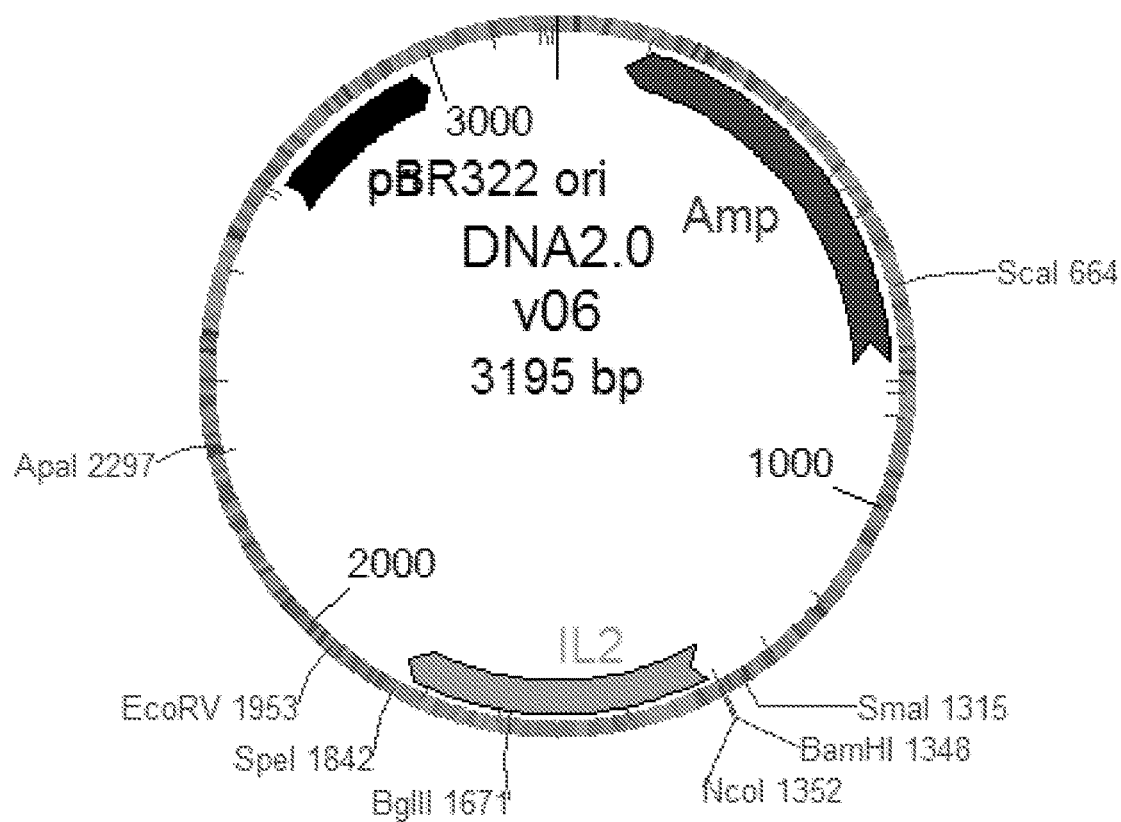
FIG. 25. DNA2.0 vector containing the ER-IL-2 cassette and having BamHI-NcoI restriction sites before the start codon and a SpeI site after the stop codon.
Figure 26:
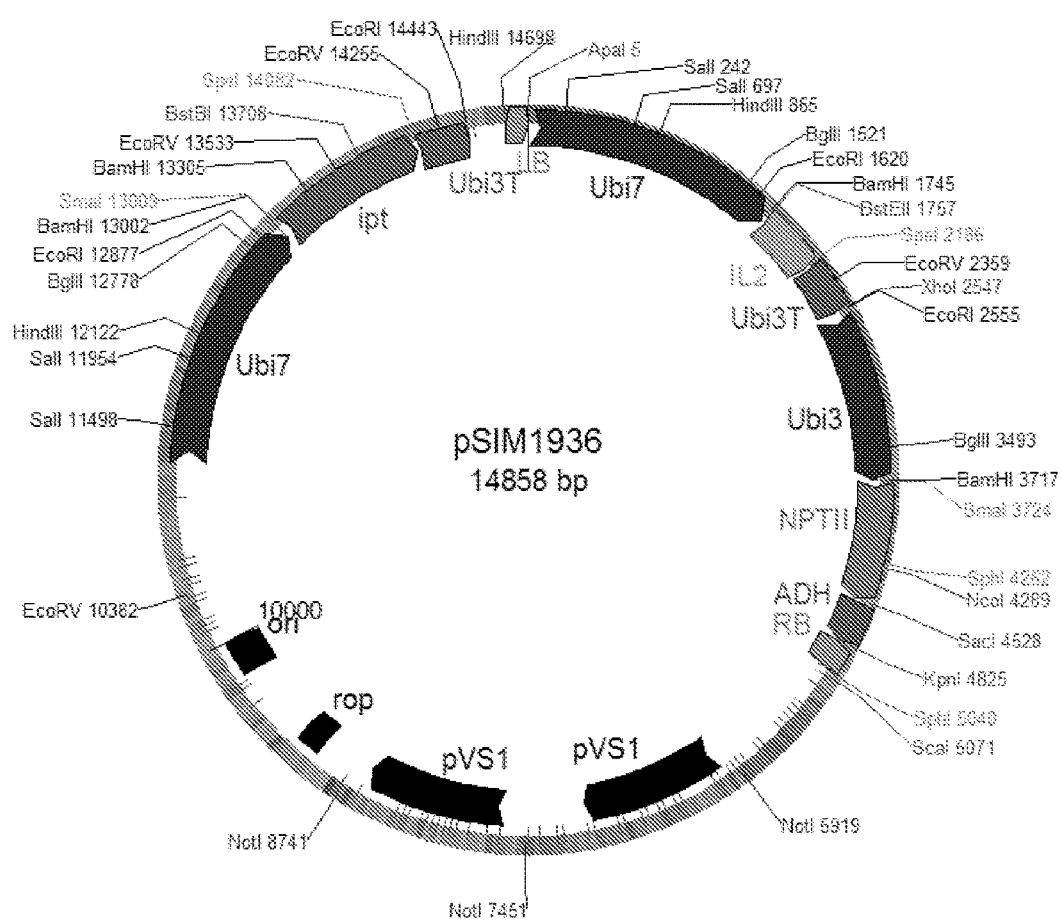
FIG. 26. Map of the vector pSIM1936 containing the histidine tagged human IL-expression cassette.
Figure 27:
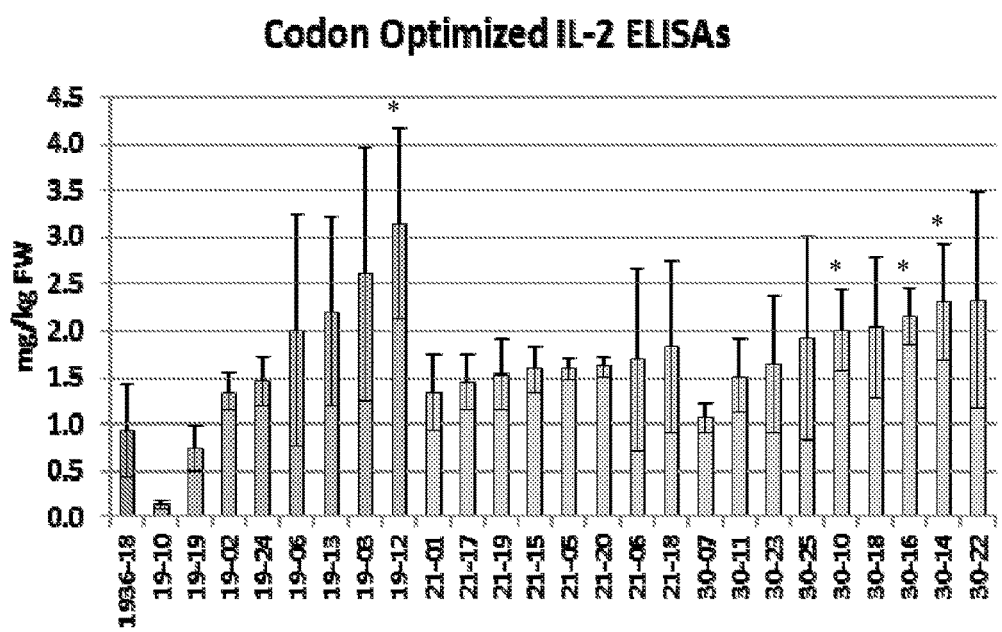
FIG. 27. IL-2 production in tubers of Bintje potato lines transformed with the pSIM1936 vector containing ER targeted, codon-optimized IL-2 variants. The 1936-18 lane represents the non-optimized positive control. For each variant, 25 independent transgenic lines were created. Each color represents the codon-optimized IL-2 variant that was used for the transformation. Each bar represents the average level of IL-2 in three individual tubers from an independent transgenic line. The results show that IL-2 production was increased 2 to 3-fold in specific transgenic lines obtained from two of the codon-optimized variants.
Figure 28:
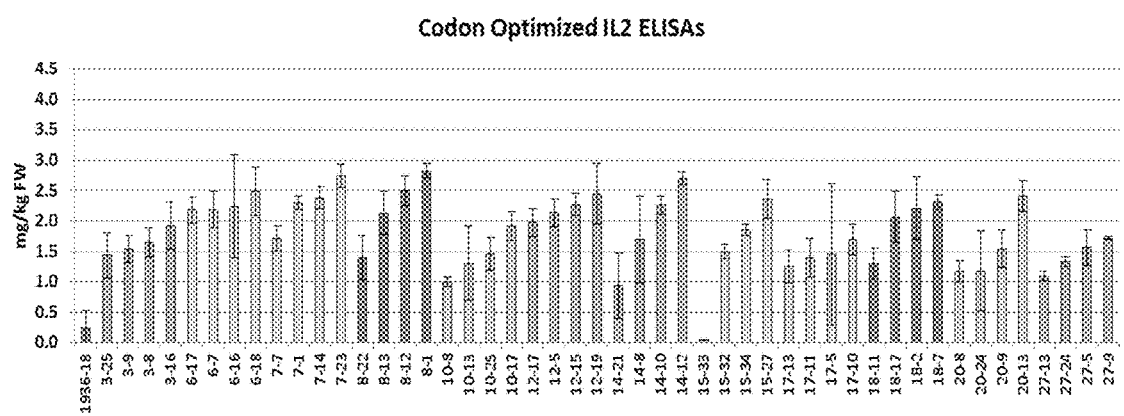
FIG. 28. IL-2 production in tubers of Bintje potato lines transformed with the pSIM1936 vector containing ER targeted, codon-optimized IL-2 variants. The 1936-18 lane represents the non-optimized positive control. For each variant, 25 independent transgenic lines were created. Each color grouping represents the codon-optimized IL-2 variant that was used for the transformation. Each bar represents the average level of IL-2 in three individual tubers from an independent transgenic line. The results show that IL-2 production was increased by 2.5 -fold in specific transgenic lines obtained from different codon variants.

Two constructs were created to compare GFP expression in potato using the EGFP gene fused to the signal peptide of GBSS (FIG. 21 and SEQ ID NO:8) or fused to the signal peptide of RuBisCo (FIG. 22 and SEQ ID NO:9). A control vector pSIM1949 (FIG. 20) was made using the EGFP gene without signal peptide as a control. Transgenic shoots growing in vitro strongly expressing GFP were selected using fluorescence microscopy. Extremely strong GFP expression was detected in the leaves of transgenic pSIM1947 plantlets, while GFP expression in pSIM1948 plantlets was slightly stronger than that of the control construct carrying the EGFP gene without signal peptide, as shown in FIG. 23. These results indicate that concomitant protein over-expression with the GBSS transit peptide and AGP silencing by convergent promoters are effective in enhancing recombinant protein production.

Example 2

Silencing of the Patatin PATB1 Gene

Figure 9:
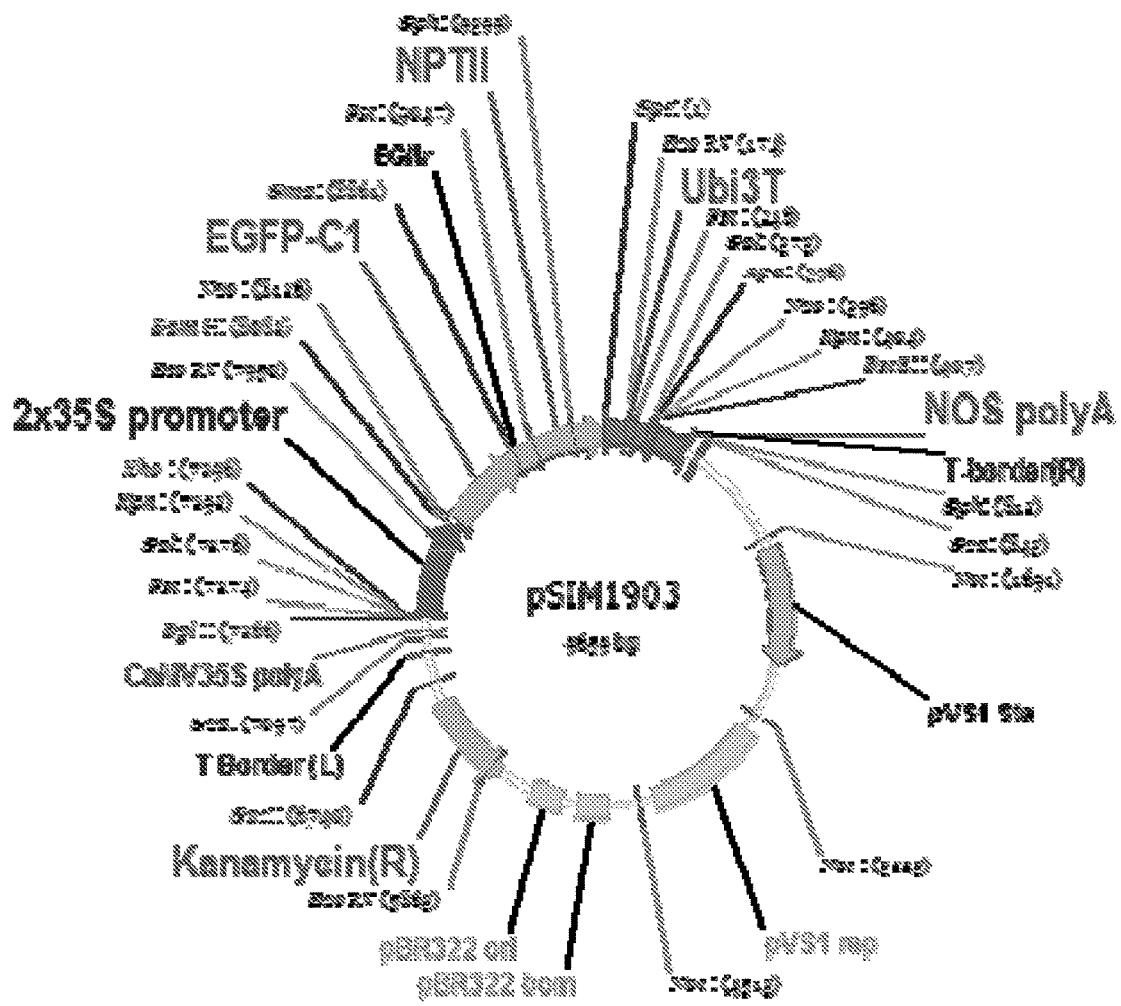
FIG. 9. Map of the control vector pSIM1903.
Figure 14:
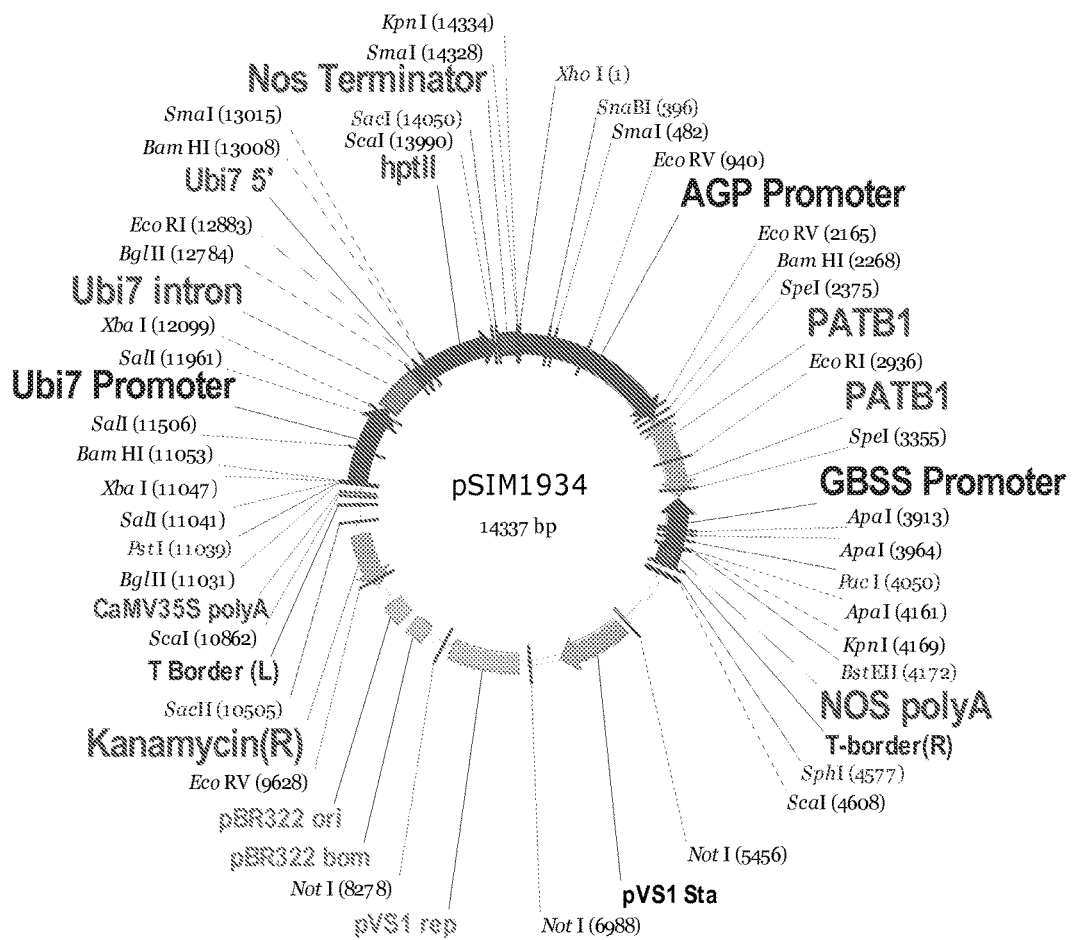
FIG. 14. Map of the vector pSIM1934 containing the patatin gene silencing cassette.
Figure 15:
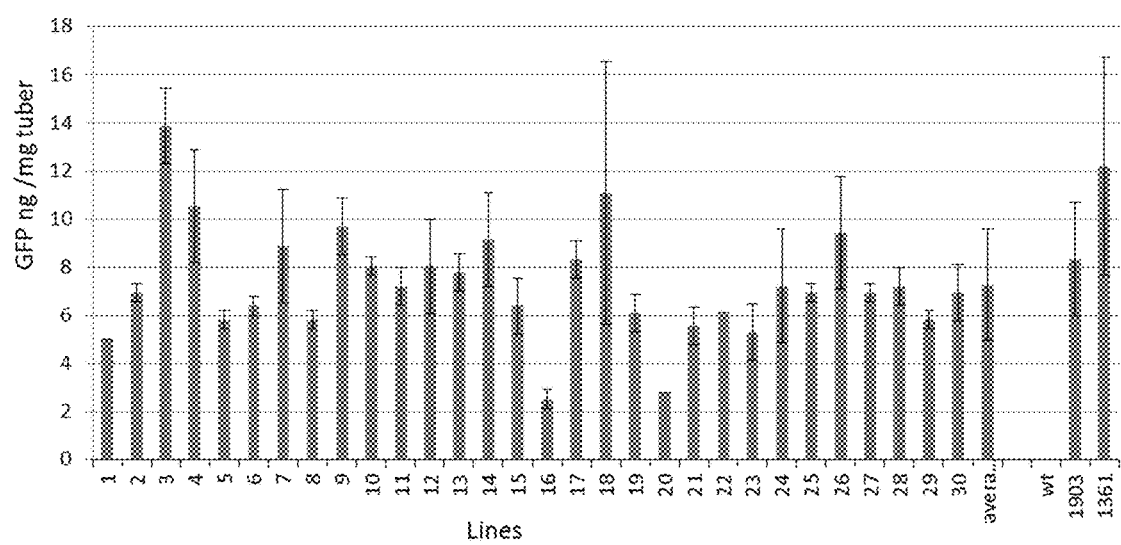
FIG. 15. GFP quantification of pSIM1934 lines. Thirty pSIM1934 transgenic lines were generated from parent material overexpressing GFP (SEQ ID NO:7), that was originally transformed with the pSIM1903 vector (FIG. 9). The lane marked 1361 denotes the empty vector control and the lane marked 1903 is the GFP parent control. GFP accumulation was not observed in any of the pSIM1934 experimental lines.
Figure 16:
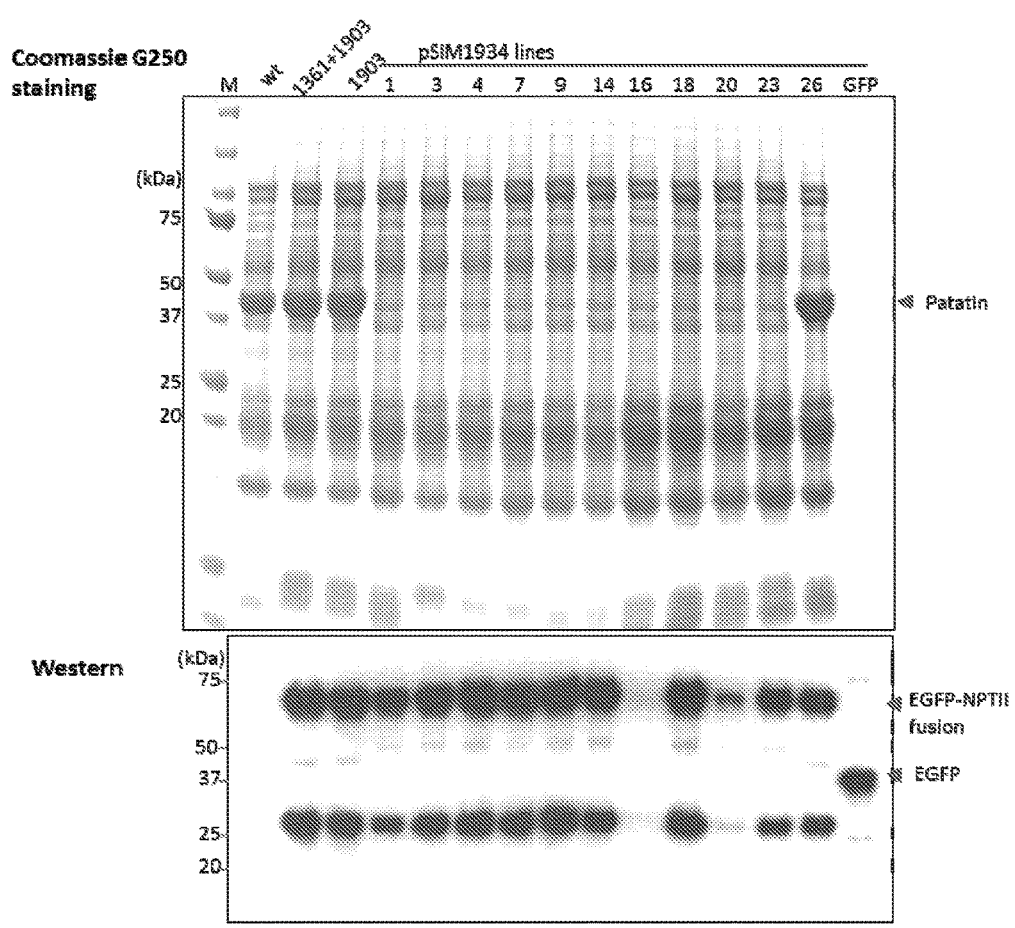
FIG. 16. SDS-PAGE and Western analyses of selected pSIM1934 lines. Thirty pSIM1934 transgenic lines were generated from parent material overexpressing GFP (SEQ ID NO:7), which was originally transformed with the pSIM1903 vector (FIG. 9). The lane marked 1903 is the GFP parent control and lane marked 1361+1903 denotes the combination of the empty vector control and the GFP parent control. In 10 lines the majority of patatin proteins (approximately 40 kDa bands) were eliminated by silencing.

Applicants have also devised nucleic acid constructs that suppress expression of the patatin gene using primers designed from the nucleotide sequence of the patatin PATB 1 gene (SEQ ID NO:3 and SEQ ID NO:4). The pSIM1934 plasmid (FIG. 14) was constructed with the goal of silencing the Solanum tuberosum patatin gene in a tuber-specific manner. Thirty transgenic lines were generated from parent material overexpressing GFP (SEQ ID NO:7) that was originally transformed with the pSIM1903 vector (FIG. 9). None of the pSIM1934 experimental lines showed increased GFP expression in tubers (FIG. 15). Further, SDS-PAGE and Western blotting analysis demonstrated that the majority of patatin proteins (approximately 40 kDa bands) were eliminated by silencing in 10 experimental lines (FIG. 16).

Example 3

Silencing of the CD4B Protease Gene

Figure 17:
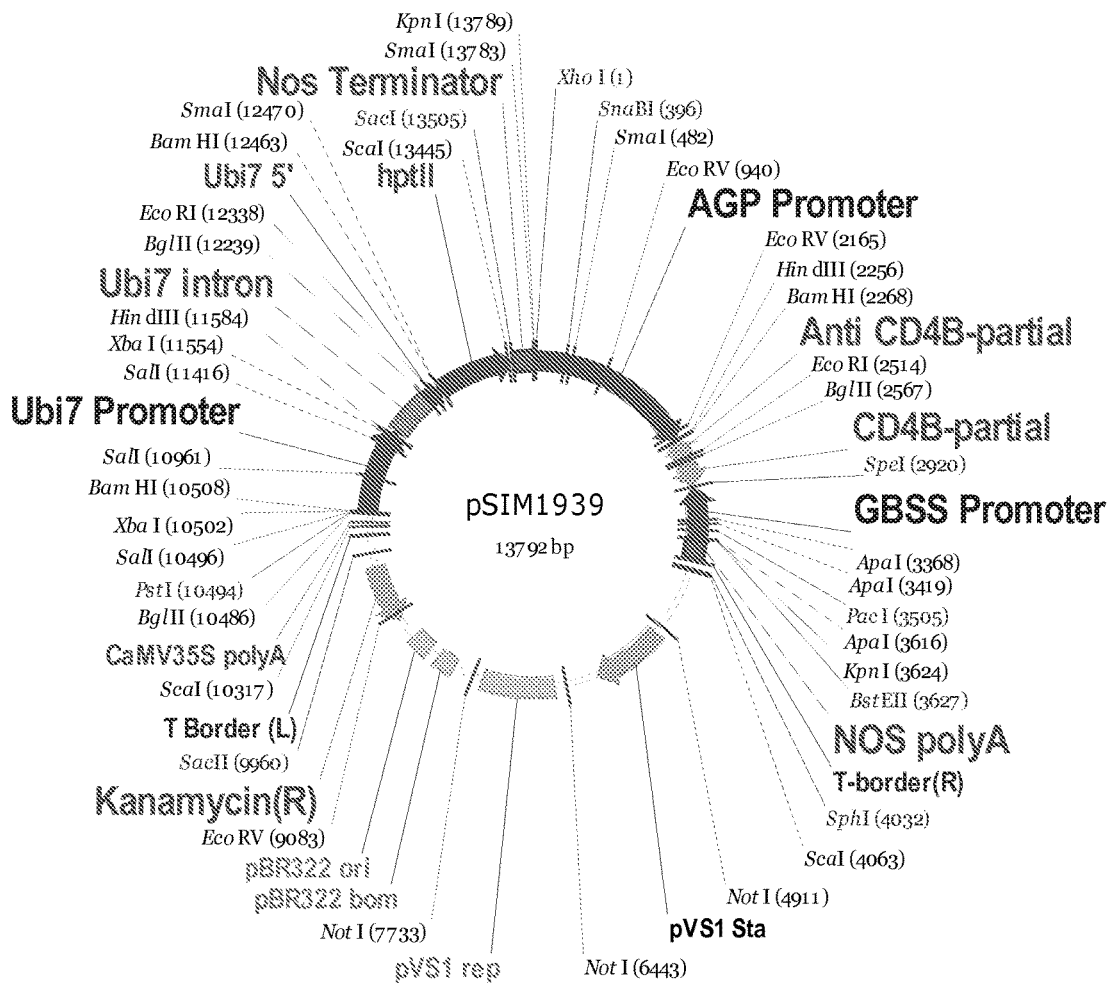
FIG. 17. Map of the vector pSIM1939 containing the CD4B silencing cassette.
Figure 18:
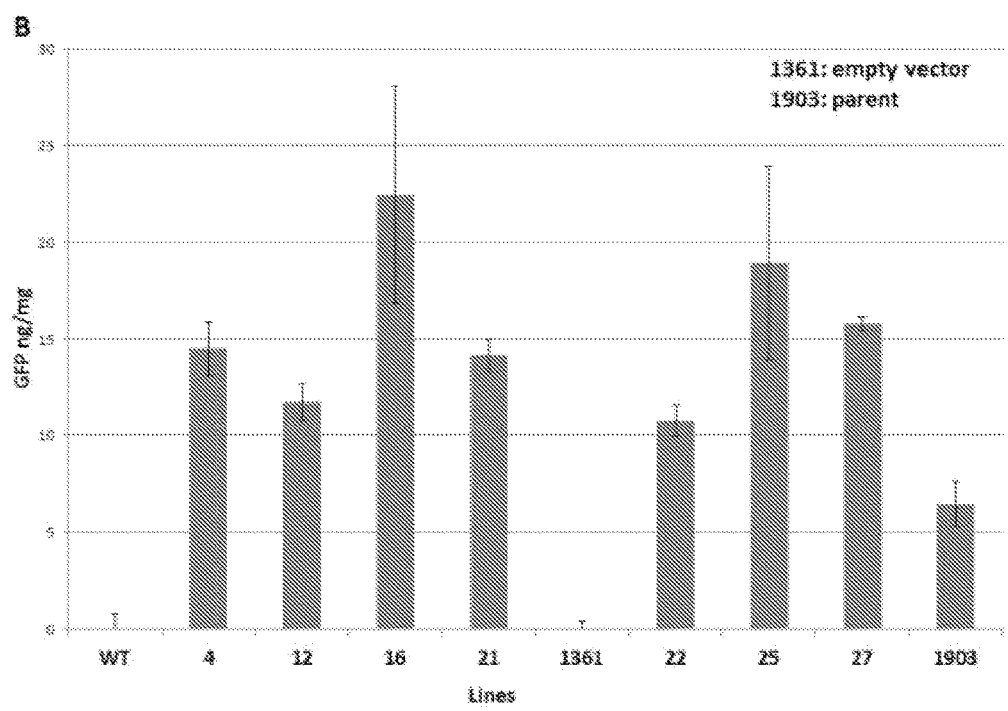
FIG. 18. GFP quantification of selected pSIM1939 lines. Twenty-six pSIM1939 transgenic lines were generated from parent material overexpressing GFP (SEQ ID NO:7), that was originally transformed with the pSIM1903 vector (FIG. 9). The lane marked 1361 denotes the empty vector control and the lane marked 1903 is the GFP parent control. Seven transgenic lines showed a 2-3-fold increase in GFP accumulation as compared to the parent line (pSIM1903).
Figure 19:
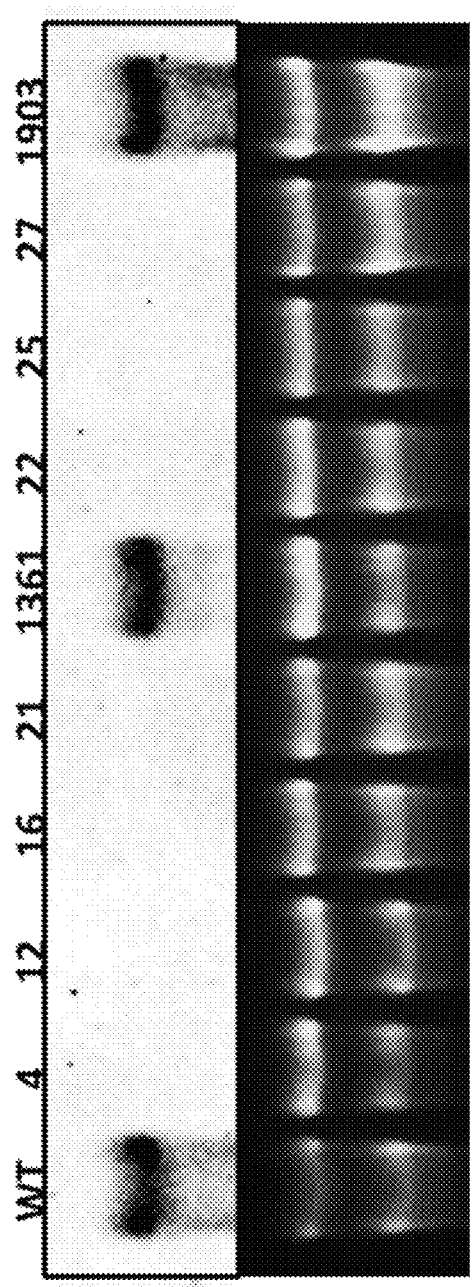
FIG. 19. Northern blot analysis of selected pSIM1939 lines. Twenty-six pSIM1939 transgenic lines were generated from parent material overexpressing GFP (SEQ ID NO:7), that was originally transformed with the pSIM1903 vector (FIG. 9). The lane marked 1361 denotes the empty vector control and the lane marked 1903 is the GFP parent control. Northern blot analysis of the seven transgenic lines that showed a 2-3-fold increase in GFP accumulation as compared to the parent line (pSIM1903) failed to detect CD4B transcript in any of the lines, thus confirming CD4B gene silencing. These results link silencing of the CD4B protease to a 2-3 fold increase in recombinant protein (GFP) production and demonstrate that tuber-specific silencing of CD4B can be used to enhance recombinant protein production.

Applicants have devised nucleic acid constructs that suppress expression of CD4B (ATP-dependent protease ATP-binding subunit clpA homolog) using CD4B specific region of cDNA sequence PGSC0003DMG402014476 in the Potato Genome Sequencing Consortium Public Data (SEQ ID NO:5 and SEQ ID NO:6). The pSIM1939 plasmid (FIG. 17) was constructed with the goal of silencing the *Solanum tuberosum* CD4B gene in a tuber-specific manner. Twenty-six transgenic lines were generated from parent material overexpressing GFP (SEQ ID NO:7) that was originally transformed with the pSIM1903 vector (FIG. 9). When analyzed for GFP accumulation in the tuber, seven transgenic lines showed a 2-3-fold increase in GFP accumulation as compared to the parent line (pSIM1903). (FIG. 18). To confirm silencing of the CD4B gene, Northern blotting analysis of the seven transgenic lines that showed a 2-3-fold increase in GFP accumulation as compared to the parent line (pSIM1903) was performed. The northern blot analysis failed to detect CD4B transcript in any of the lines, thus confirming CD4B gene silencing. These results link silencing of the CD4B protease to a 2-3 fold increase in recombinant protein (GFP) production and demonstrate that tuber-specific silencing of CD4B can be used to enhance recombinant protein production.

Example 4

Overexpression of Human Interleukin 2 (IL-2) in Potato

Applicants have devised nucleic acid constructs that overexpress a gene of interest in potato. The pSIM1936 plasmid (FIG. 26) was construed with the goal to overexpress human interleukin 2 (IL-2) in potato plants. Expression Cassettes A truncated version of the human interleukin 2 (IL-2) gene was placed between a *Solanum tuberosum* patatin ER transit peptide (N-terminus) and an ER retention signal (C-terminus) (FIG. 24). Forty-eight codon-optimized variants of the IL-2 insert containing the ER transit peptide, the IL-2 gene and the ER retention signal (v1-v48) were created in cloning vectors by DNA 2.0 (Menlo Park, Calif., USA). Each variant had BamHI-NcoI restriction sites before the start codon and a SpeI site after the stop codon (FIG. 25). For plant expression, the entire ER-targeted gene cassette was inserted into the pSIM1936 plasmid between the *Solanum tuberosum* ubiquitin promoter (Ubi7) and the *Solanum tuberosum* ubiquitin terminator (Ubi3T) (FIG. 26). Six expression vectors containing the different codon-optimized IL-2 inserts were created in a 1-step, 3-piece ligation. Each variant had a different codon-optimized IL-2 insert (v19, v21, v30, v43, v45, v47). Twelve additional expression vectors containing additional codon-optimized IL-2 inserts were created in a 2-step ligation using a modified pSIM1936 plasmid, with the second Spe I site removed via PCR mutagenesis. An empty vector control was created by removing the ApaI-XhoI fragment (2,542 bp) containing the entire expression cassette from promoter to terminator. The 5' overhangs were filled in using Klenow fragment (New England BioLabs, Inc, Ipswich, Mass., USA), followed by a blunt-end ligation with T4 DNA Ligase (Thermo Scientific, Pittsburgh, Pa., USA).

Plant Transformation and Growth

Bintje stock plants were maintained in Magenta boxes containing half-strength M516 salts and vitamins (PhytoTechnology, Shawnee Mission, Kans., USA), 1.5% sucrose, 2.5 g/l calcium gluconate and 2 g/l gelrite (pH 5.7). *Agrobacterium* strain LBA4404 was grown overnight at 28° C. in LB medium (20 g/l LB broth) containing 50 mg/l kanamycin and 100 mg/l streptomycin. The resulting cultures were precipitated at 9,500 rpm for 10 min and resuspended in M404 salts and vitamins (PhytoTechnology) with 3% sucrose (pH 5.7) to obtain a cell density with an OD600 of 0.2. Bintje internode segments of 4-6 mm were cut from 4-week old stock plants, infected with the *Agrobacterium* suspension containing the different expression vector variants for 10 min and then aspirated off. The explants were then transferred to co-cultivation medium (1/10 M404, 3% sucrose and 7 g/l agar (pH 5.7)) for 2 days before being transferred to callus induction medium (M404, 3% sucrose, 7 g/l agar, 2.5 mg/l zeatin riboside, 0.1 mg/l NAA, 150 mg/l timentin and 100 mg/l kanamycin (pH 5.7)). After one month, the explants were transferred to shoot induction medium (M404, 3% sucrose, 7 g/l agar, 2.5 mg/l zeatin riboside, 0.3 mg/l gibberellic acid, 150 mg/l timentin and 100 mg/l kanamycin (pH 5.7)). Rooting assays were performed twice using selective rooting medium (half-strength M516, 1.5% sucrose, 100 mg/l kanamycin, 100 mg/l timentin and 2 g/l gelrite (pH 5.7)). Plant material was maintained in a Percival growth chamber under a 16 h photoperiod at 24° C. Twenty-five phenotypically normal, kanamycin-resistant shoots were selected for growth in the greenhouse. Rooted plants were then placed in 2-gallon pots with Sunshine Mix #1 (Sun Gro Horticulture, Agawam, Mass., USA) and fertilized at 2-week intervals with full strength Miracle Grow (1 Tbs/gallon water) 3 times. One cup of fertilizer solution was used per 1 gallon pot (2 cups for 2 gallon pots). Semi-mature tubers were obtained after 3 months of growth in a temperature controlled (18° C. minimum/27° C. maximum) greenhouse. During the summer, daylight/length was not supplemented.

IL-2 Quantification

For ELISAs and IL-2 production determination, a 50 mg sample was extracted from the center of the tuber utilizing a 4-mm cork borer. The sample was then homogenized in a 1.5 ml centrifuge tube with 250 μl of assay buffer using a pellet pestle. Homogenization buffers and samples were kept on ice at all times and centrifuged at 4° C. for 20 min at 9500 rpm. The ELISAs were performed according to the BD OptEIA human IL-2 ELISA Kit II protocol (BD Biosciences, San Jose, Calif., USA). Samples were read in 96-well plates by a Multimode Detector DTX 880 (Beckman Coulter). To screen through each independent line, one sample was taken from a single tuber. The lines with the highest level of IL-2 production were then resampled from 3 individual tubers. Absorbance was read at 450/8 nm.

Results

FIG. 27 shows IL-2 production in tubers from independently transformed lines of Bintje potatoes for 3 of the 6 codon-optimized IL-2 variants tested (v19, v21 and v30). 1936-18 was the non-optimized positive control. For each variant, 25 independent transgenic lines were created. Each color grouping represents the codon-optimized IL-2 variant that was used for the transformation. Each bar represents the average level of IL-2 in three individual tubers from an independent transgenic line. The results show that IL-2 production was increased 2 to 3-fold in specific transgenic lines obtained from different codon variants. In additional experiments (data not shown), IL-2 production increased up to 11 fold in specific transgenic lines.

Similarly, FIG. 28 shows IL-2 production in tubers from independently transformed lines of Bintje potatoes for 12 codon-optimized IL-2 variants. 1936-18 was the non-optimized positive control. For each variant, 25 independent transgenic lines were created. Each color represents the codon-optimized IL-2 variant that was used for the transformation. Each bar represents the average level of IL-2 in three individual tubers from an independent transgenic line. The results show that IL-2 production was increased by 2.5 -fold in specific transgenic lines obtained from different codon variants.

Example 5

Overexpression of Other Genes of Interest in Potato

Figure 3:
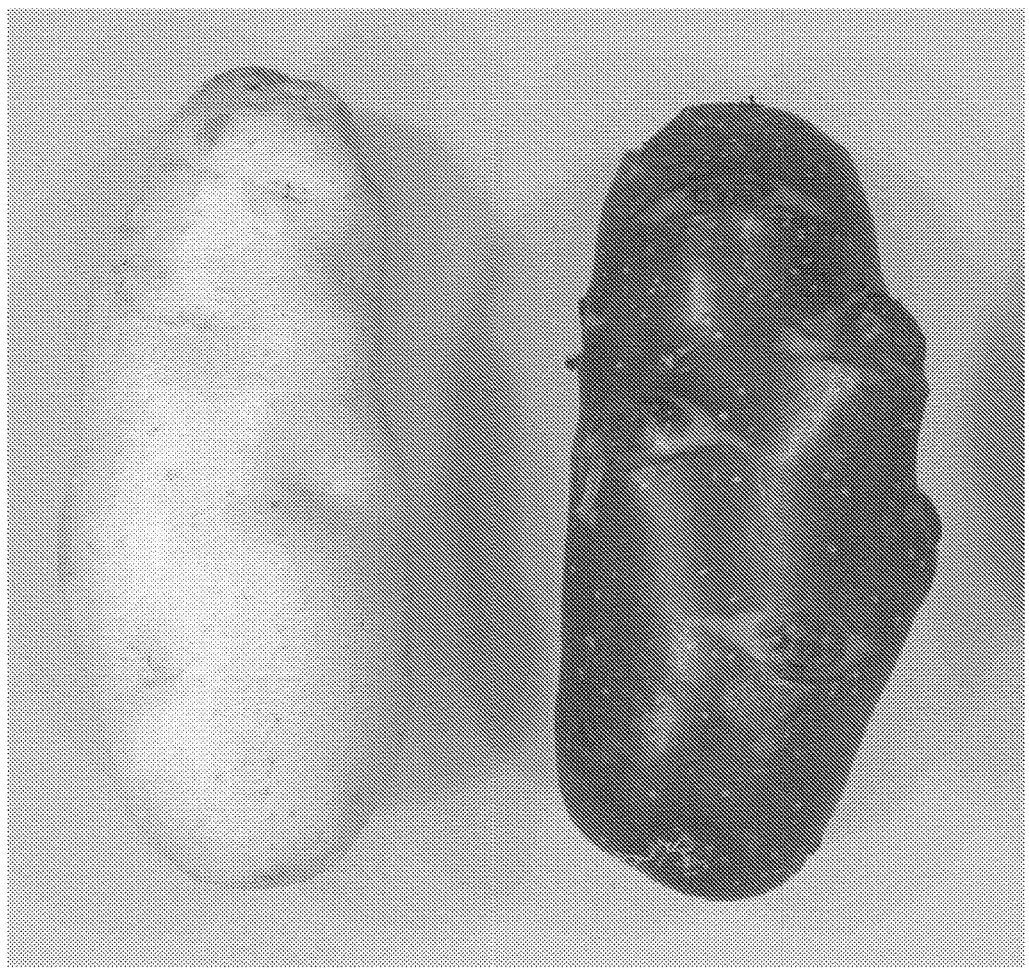
FIG. 3. Tubers from untransformed potato (left) and potato overexpressing the chlorogenic acid inducer (CAI) gene (right) that triggers a four-fold increase in the synthesis of chlorogenic acid, anthocyanins and flavonols.
Figure 4:
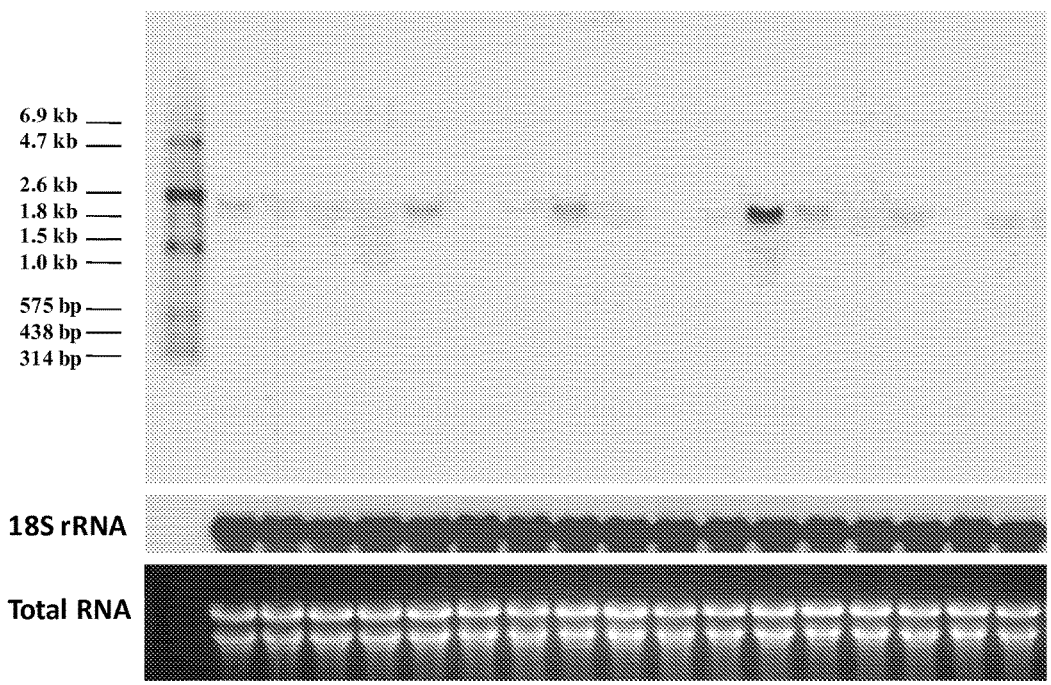
FIG. 4. Northern blot analysis of PPO5 gene silencing. Total RNA (20 ug) was isolated from greenhouse-grown tuber tissues of transgenic plants in which the PPO5 gene was silenced and controls, and hybridized with the PPO5 probe (upper panel) and the internal benchmark 18S rRNA probe (middle panel). The predicted size of the transcript was 1.95-kb (see Genbank Accession U22921). The lower panel shows the amounts of total RNA as visualized with ethidium bromide (EB). EC, FC, JC, GC, and HC are control samples from untransformed conventional varieties. Individual transgenic event samples are labeled above each lane. The data demonstrate that black spot bruise tolerance is linked to effective silencing of the PPO5 gene (see for instance, Rommens, C. M., Ye, J., Richael, C., Swords, K., 2006, J Agric Food Chem 54:9882-9887).

In other embodiments, Applicants demonstrated that overexpression of chlorogenic acid inducer (CAI) gene stimulates a four-fold increase in chlorogenic acid, as well as anthocyanins and flavonols (FIG. 3).

Figure 5:
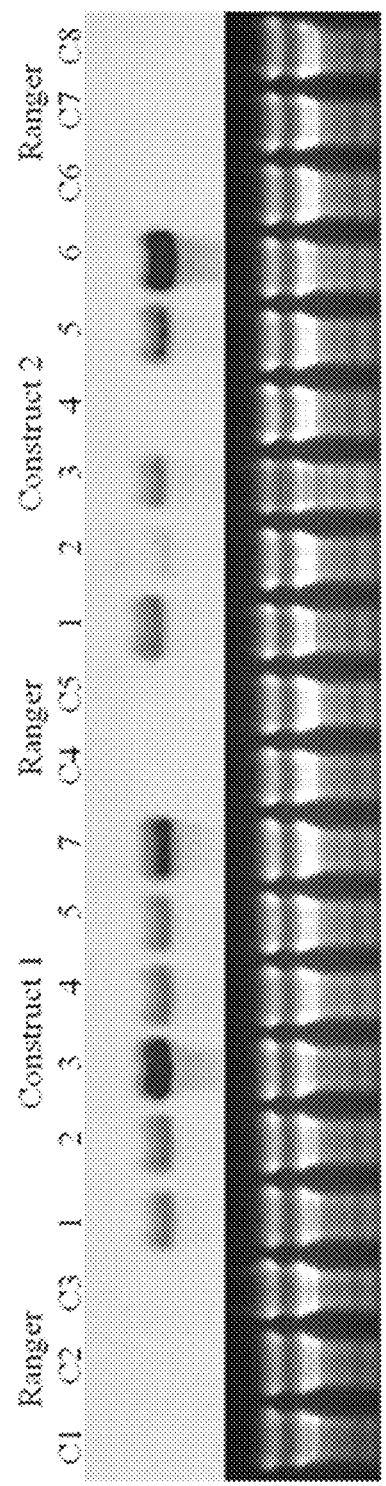
FIG. 5. Northern blot analysis of VTC2 gene expression in transgenic potato. Total RNA (20 ug) was isolated from greenhouse-grown tuber tissues of transgenic events and controls (C1-C8) and hybridized with the VTC2 probe (upper panel). The lower panel shows the amounts of total RNA as visualized with ethidium bromide (EB).

Similarly, a vitamin C biosynthetic (VTCB) gene was overexpressed in potatoes using the methods of the invention (FIG. 5).

Figure 6:
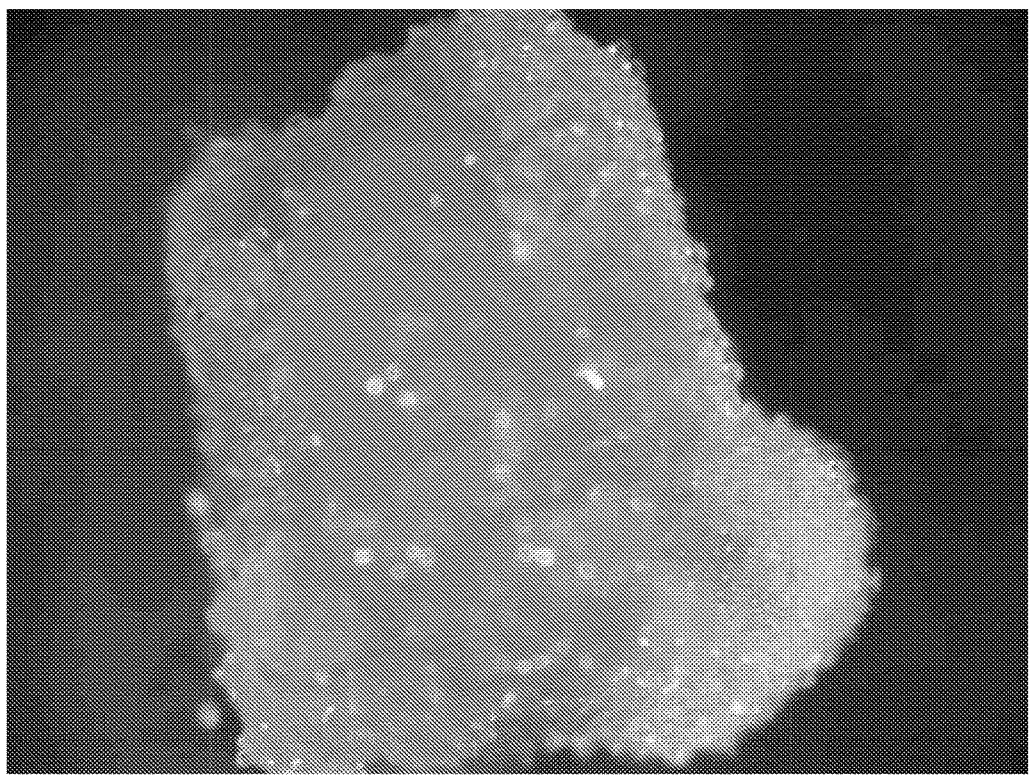
FIG. 6. GFP gene expression in potato stem explants. Potato plants were transformed with the Green Fluorescent Protein (GFP) gene. High level GFP expression could be seen in transgenic potato plants upon overexpression with a strong constitutive promoter.
Figure 7:
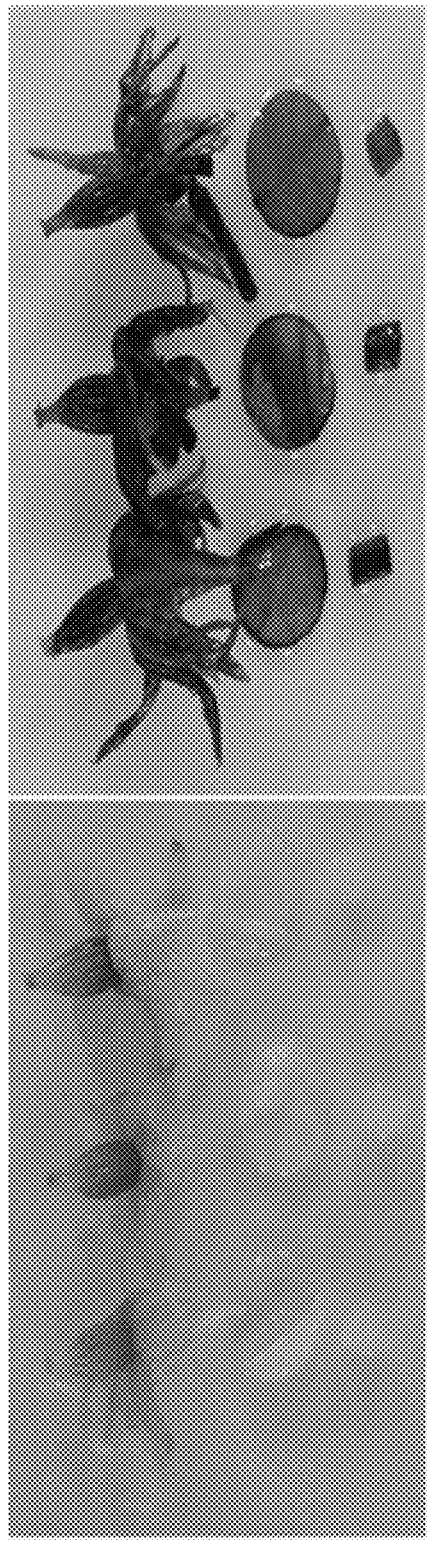
FIG. 7. High-level GUS gene expression in transgenic potato flowers, leaves, and stems as compared to untransformed potato flowers, leaves and stems.
Figure 8:
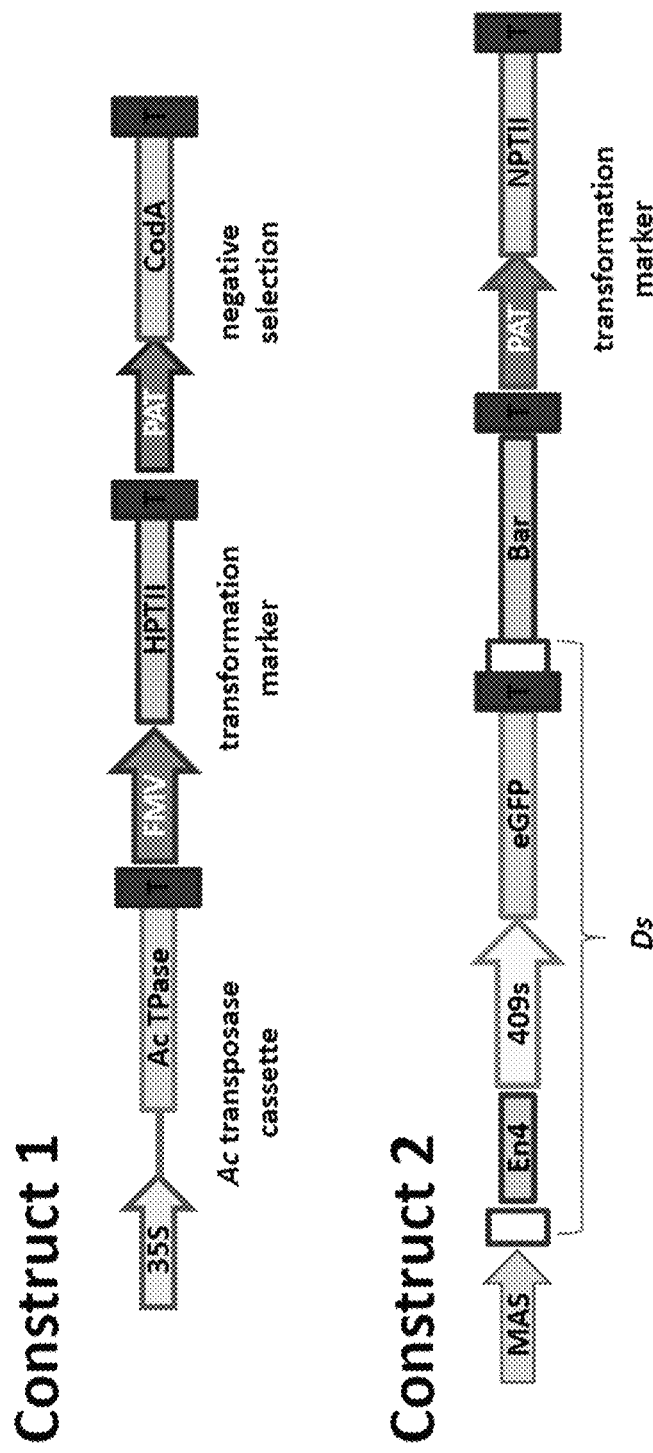
FIG. 8. Co-transformation constructs for transposition of a gene of interest (e.g. GFP) into sites that support optimal gene expression.

Likewise, GFP gene expression remarkably increases in potato stem explants upon overexpression with a strong constitutive promoter (FIG. 6) and high-level GUS gene expression may be obtained in potato flowers, leaves, and stems according to the methods of the invention (FIG. 7).

Example 6

Overexpression of P19 which is a Suppressor of RNA Silencing

The expression of heterologous proteins in transgenic plants could be diminished by the activation of post-transcriptional gene silencing (PTGS) in the plant host. The expression of plant virus suppressors of gene silencing, such as P19, could reduce this response in leaves, increasing by several fold the expression levels of heterologous proteins (Circelli et al, 2010 Bioengineered Bugs 1:221-224). Surprisingly, the Applicants found that expression of P19 increased the production of GFP in tubers as well.

Figure 10:
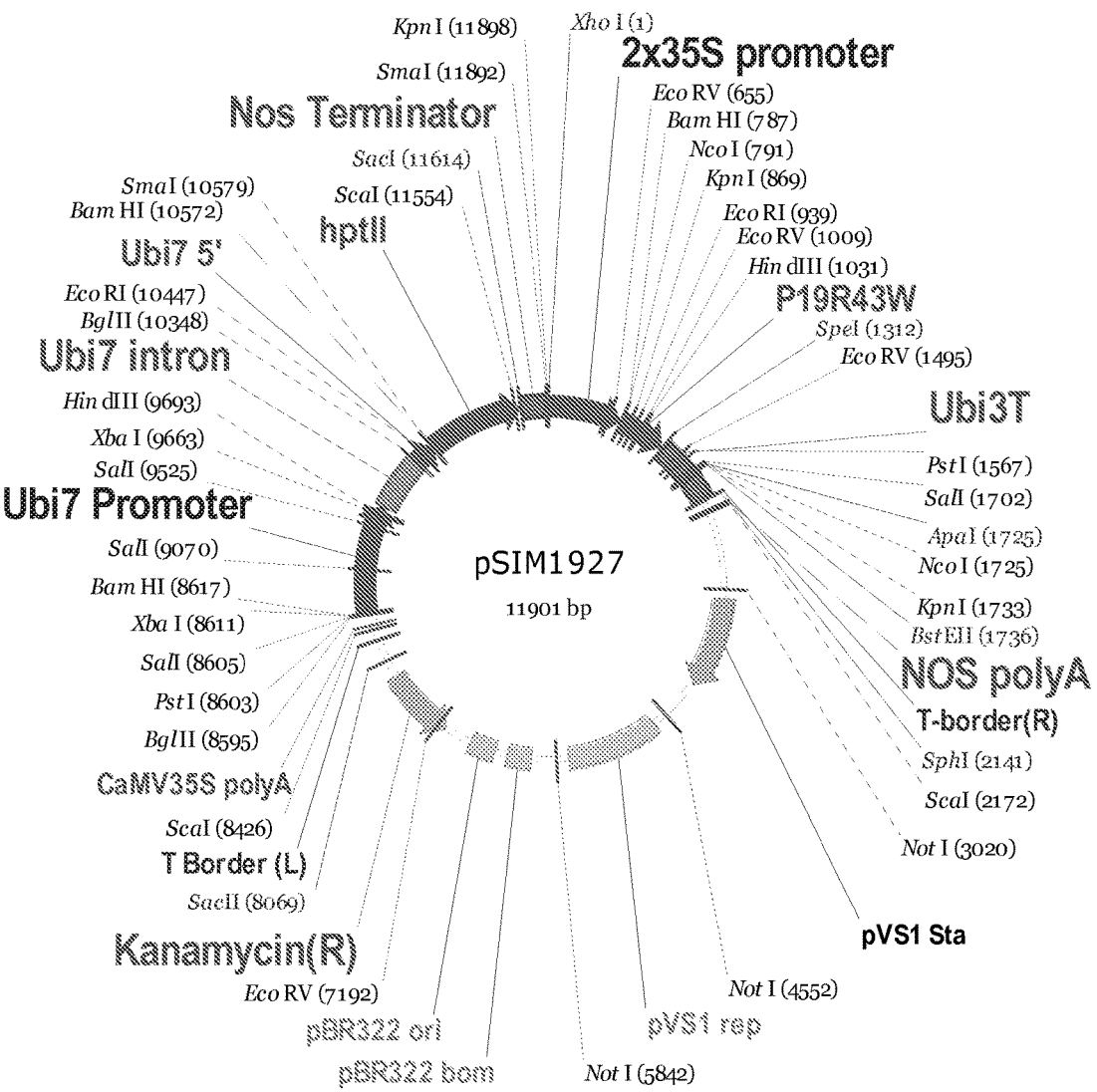
FIG. 10. Map of the vector pSIM1927 containing a 2×35S promoter-driven P19R43 (SEQ ID NO:2) P19 mutant within the T-DNA borders.
Figure 11:
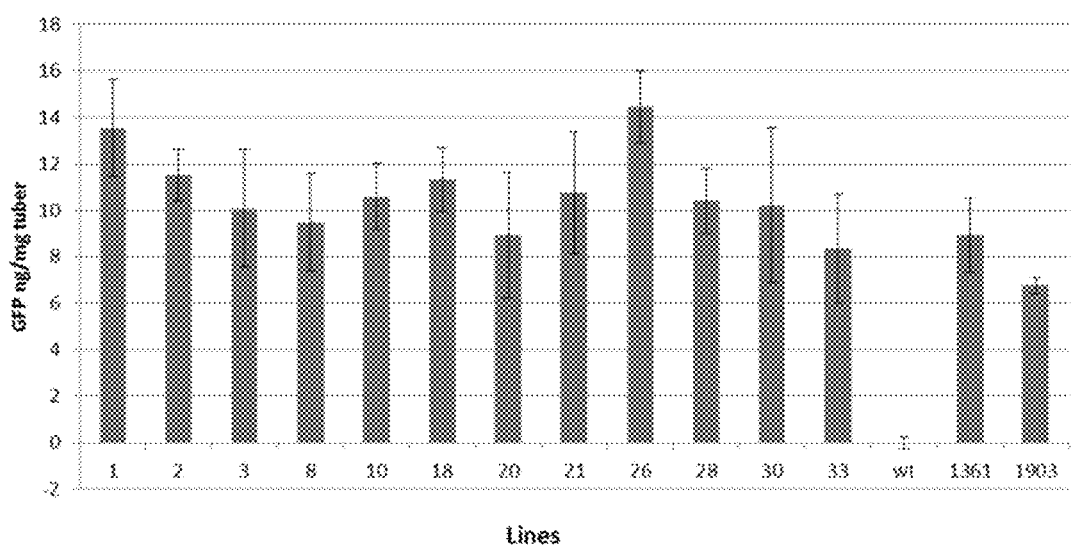
FIG. 11. GFP quantification of selected pSIM1927 lines. Thirty-three lines over-expressing P19R43 were generated from parent material overexpressing GFP (SEQ ID NO:7) that was originally transformed with the pSIM1903 vector (FIG. 9). All lines grew normally in a greenhouse with no obvious pleiotropic effects. The transgenic lines were visually screened for tuber-specific GFP accumulation as compared to the empty vector line (pSIM1361) and the parent line (pSIM1903). Twelve lines showing high GFP expression were selected for GFP quantification. A 20 to 60% increase in GFP amount as compared to the amount in the empty vector line was detected in 10 of the 12 transgenic lines.
Figure 12:
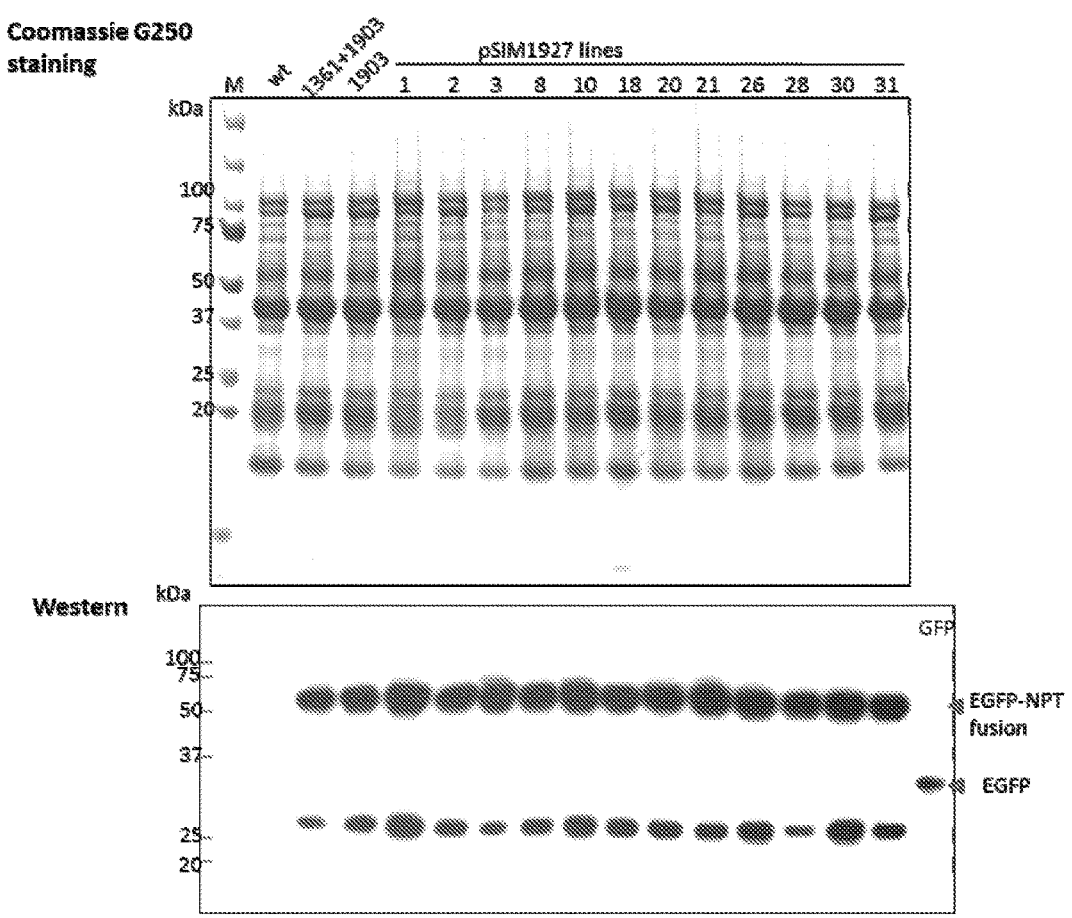
FIG. 12. Western blot analysis of selected pSIM1927 lines. Thirty-three lines over-expressing P19R43 were generated from parent material overexpressing GFP (SEQ ID NO:7) that was originally transformed with the pSIM1903 vector (FIG. 9). All lines grew normally in a greenhouse with no obvious pleiotropic effects. The transgenic lines were visually screened for tuber-specific GFP accumulation as compared to the empty vector line (pSIM1361) and the parent line (pSIM1903). Twelve lines showing high GFP expression were selected for Western blot analysis. A 20 to 60% increase in GFP amount as compared to the amount in the empty vector line was detected in 10 of the 12 transgenic lines.

The pSIM1927 plasmid (FIG. 10) was constructed with a 2×35S promoter-driven P19R43 (SEQ ID NO:2) P19 mutant within the T-DNA borders. Thirty-three lines over-expressing P19R43 were generated from parent material overexpressing GFP (SEQ ID NO:7) that was originally transformed with the pSIM1903 vector (FIG. 9). All lines grew normally in a greenhouse with no obvious pleiotropic effects. The transgenic lines were visually screened for tuber-specific GFP accumulation as compared to the empty vector line (pSIM1361) and the parent line (pSIM1903). Twelve lines showing high GFP expression were selected for GFP quantification, western blot analysis and northern blot analysis. A 20 to 60% increase in GFP amount as compared to the amount in the empty vector line was detected in 10 of the 12 transgenic lines (FIG. 11 and FIG. 12).

Figure 13:
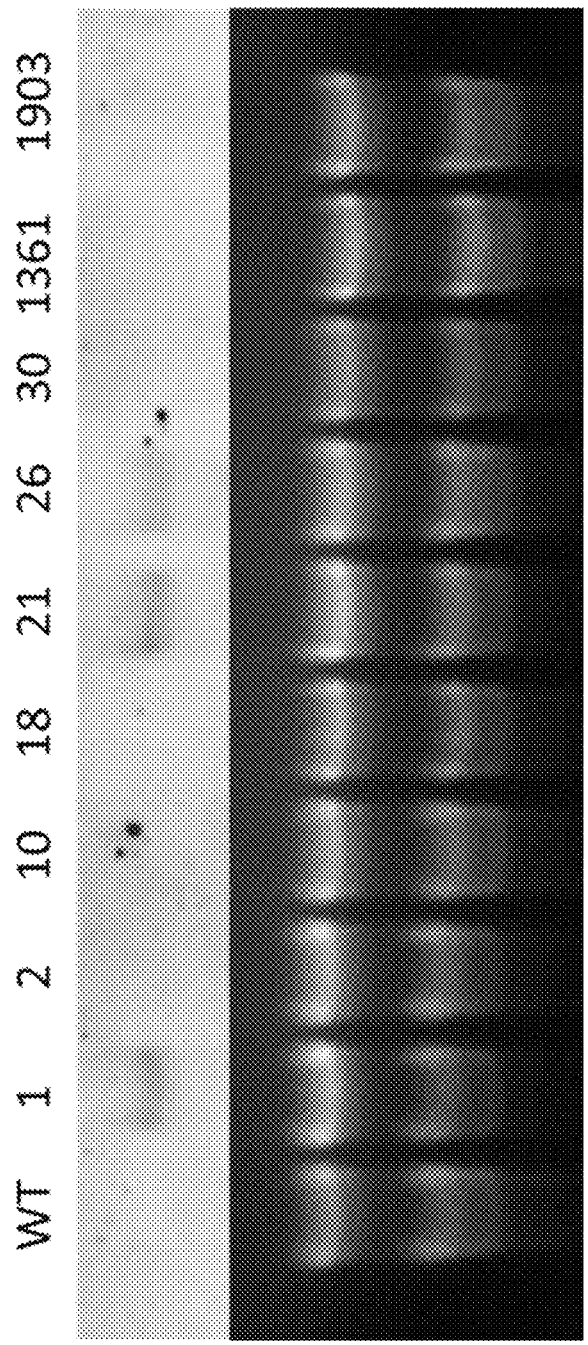
FIG. 13. Northern blot analysis of selected pSIM1927 lines. Thirty-three lines over-expressing P19R43 were generated from parent material overexpressing GFP (SEQ ID NO:7) that was originally transformed with the pSIM1903 vector (FIG. 9). All lines grew normally in a greenhouse with no obvious pleiotropic effects. The transgenic lines were visually screened for tuber-specific GFP accumulation as compared to the empty vector line (pSIM1361) and the parent line (pSIM1903). To confirm expression of the P19 gene, RNA from the seven lines showing high GFP expression was analyzed with a P19 probe. P19 transcript was detected in three lines including the two lines with the highest GFP expression. These results, which link the expression of the mutated p19 suppressor of RNA silencing with the elevated expression of GFP protein, demonstrate that suppression of P19, a suppressor of RNA silencing, enhances protein production in plants.

To confirm expression of the P19 gene, RNA from the seven lines showing high GFP expression was analyzed with a P19 probe. P19 transcript was detected in three lines including the two lines with the highest GFP expression (FIG. 13). These results, which link the expression of the mutated p19 suppressor of RNA silencing with the elevated expression of GFP protein, demonstrate that suppression of P19, a suppressor of RNA silencing, enhances protein production in plants.

Example 7

Concomitant Overexpression of GFP and Patatin and CD4B Gene Suppression

An expression cassette was constructed comprising the components for suppressing patatin and CD4B gene expression. About thirty transgenic lines were generated by transforming parent material overexpressing GFP with a vector containing the expression cassette. Increased GFP production was observed by GFP accumulation analysis in the tubers of the transgenic plants, when compared to untransformed lines and transgenic lines with either patatin or CD4B suppressed alone. SDS-PAGE and Western blotting analysis demonstrated that the majority of patatin proteins (approximately 40 kDa bands) were eliminated. Northern blotting analysis showed that the CD4B transcript was suppressed. GFP production was enhanced by simultaneously suppressing the gene expression of patatin and CD4B.

Example 8

Concomitant Overexpression of P19 and GFP and Patatin Gene Suppression

An expression cassette was constructed comprising the components for suppressing patatin gene expression and overexpressing P19. About thirty transgenic lines were generated by transforming parent material overexpressing GFP with a vector containing the expression cassette. GFP production was increased in the tubers of the transgenic plants, when compared to untransformed lines and transgenic lines in which the patatin gene alone had been suppressed. SDS-PAGE and Western blotting analysis confirmed patatin gene suppression. To confirm expression of the P19 gene, RNA from the lines showing high GFP expression was analyzed with a P19 probe.

Example 9

Concomitant Overexpression of GFP and P19 genes, and Patatin and CD4B gene Suppression An expression cassette was constructed comprising the components to overexpress P19 and GFP, and suppress both patatin and CD4B genes. About thirty transgenic lines were generated by transforming parent material overexpressing GFP, with a vector containing the expression cassette. GFP production in the tubers of the transgenic plants was increased in the tubers of the transgenic plants, when compared to untransformed lines and transgenic lines in which the patatin gene alone had been suppressed (Example 8), or GFP alone, but not P19, had been over-expressed (Example 7).

Example 10

Effect of Gene Silencing and Overexpression Strategies on Protein Production in Potato Tubers Quantification of the GFP reporter gene was used to determine the effect of various gene silencing and overexpression strategies on recombinant protein production in potato tubers. The silencing and over-expression strategies were as follows: (a) silencing of CD4B alone; expression of GFP was driven by the 35S promoter; (b) silencing of CD4B and patatin; expression of GFP was driven by the 35S promoter; (c) silencing of CD4B and patatin and overexpression of P19; expression of GFP was driven by the 35S promoter; (d) silencing of AGP; expression of GFP was targeted by the GBSS transit peptide and driven by the 35S promoter; (e) silencing of AGP; expression of GFP was targeted by the Rubisco transit peptide and driven by the 35S promoter; (f) silencing of AGP; expression of GFP was driven by the 35S promoter. The GFP pSIM1903 construct in which expression of GFP was driven by the 35S promoter was used as control. These strategies are summarized in Table 2.

TABLE 2

| pSIM | Strategy | Description |
|---|---|---|
| 1903 | 2x35S: eGFP | Control |
| 1903-2 + 1951 | [2x35S: eGFP] + [Ubi7: sCD4B] | ATP-dependent CLP protease ATP-binding subunit |
| 1903-2 + 1952 | [2x35S: eGFP] + [AGP: sCD4B/patatin] | Tuber-specific silencing of CD4B & patatin |
| 1903-2 + 1953 | [2x35S: eGFP] + [2x35S: P19 + AGP: sCD4B/patatin] | P19: Tobacco bushy stunt virus silencing suppressor |
| 1947 | 2x35S: GBSS$^{TP}$-eGFP + GBSS->sAGP<-AGP | Granular bound starch synthase transit peptide + ADP glucose pyrophosphorylase silencing |
| 1948 | 2x35S: Rbcs$^{TP}$-eGFP + GBSS->sAGP<-AGP | Rubisco transit peptide + ADP glucose pyrophosphorylase silencing |
| 1950 | 2x35S: eGFP + GBSS->sAGP<-AGP | ADP glucose pyrophosphorylase silencing only |
| 1949 | 2x35S: eGFP | Control |

Plant Transformation and Growth

Bintje stock plants were maintained and transformed as described in Example 4, except that the *Agrobacterium* suspension contained different constructs as described in Table 2. For transformation of the pSIM1903-2 parent line, hygromycin selection was used at 5 mg/L.

Protein Quantification

For GFP quantification, 25 lines were analyzed for each variant, except for constitutive CD4B silencing, where 10 lines were analyzed. A 50 mg sample was extracted from the center of the tuber utilizing a 4-mm cork borer. The sample was then homogenized in a 1.5 ml centrifuge tube with 250 μl of assay buffer using a pellet pestle. Homogenization buffers and samples were kept on ice at all times and centrifuged at 4° C. for 20 min at 9500 rpm. GFP quantification was performed according to the BioVision Kit (#K815-100) protocol (BioVision Inc., Milpitas, Calif., USA). Samples were read in 96-well plates by a Multimode Detector DTX 880 (Beckman Coulter). Absorbance was read at 450/8 nm.

Results

Figure 29:
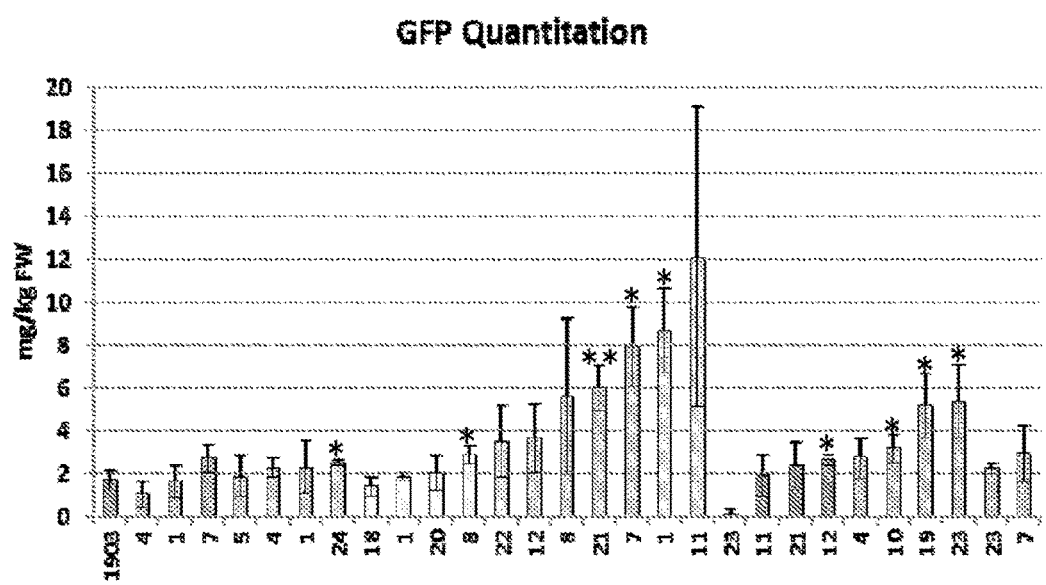
FIG. 29 shows the effect of different silencing, over-expression and targeting strategies on heterologous protein production as measured by GFP expression. 25lines were analyzed for each strategy, except for CD4B silencing, where 10 lines were analyzed. Each bar represents three individual tubers that were analyzed for GFP expression. Each group corresponds to a different silencing, over-expression or targeting strategy as follows: on the X-axis from left, to right, the single bar labeled 1903: control parent line (pSIM1903) carrying the 2,times.35S::EGFP cassette, the three bars labeled 4//1//7: silencing of CD4B. The four bars labeled 5//4//1//24: silencing of CD4.B and patatin. The four bars labeled. 18//1//20//8: silencing CD4B and patatin and over-expression of P19, The seven bars labeled 22//12//8//21//7//1//11: silencing of AGP using a GBSS promoter and a convergent AGP promoter; GFP expression was targeted to the plastids by the granule-bound starch synthase (GBBS) transit peptide. The four bars labeled 23//11//21//12: silencing of AGP using a GBSS promoter and a convergent AGP promoter; GFP expression was targeted to the chloroplasts by the RuBisCo transit peptide. The four bars labeled 4//10//19//23: silencing of AGP using a GBSS promoter and a convergent AGP promoter. The two bars labeled 23//7: control line (pSIM1949) carrying the 2.times.35S::EGFP cassette. Silencing of CD4B and patatin or CD4B alone only slightly enhanced protein levels compared to the GFP control. Silencing of AGP using a GBSS promoter and a convergent AGP promoter while driving GFP expression with the granule-bound starch synthase (GBBS) transit peptide significantly increased protein level, up to a 4- to 6-fold increase, Silencing of ADP-glucose pyrophosphorylase (AGP) while driving GFP expression with the rubisco (Rbcs) targeting peptide led to significant protein increase only in one line. Silencing of the ADP-glucose pyrophosphorylase (AGP) resulted in a significant increase in protein expression, with a 3-fold increase in some of the lines.

FIG. 29 shows the effect of different silencing, over-expression and targeting strategies on heterologous protein production as measured by GFP expression. 25 lines were analyzed for each strategy, except for CD4B silencing, where 10 lines were analyzed. Each bar represents three tubers that were analyzed for GFP expression. Silencing of CD4B alone or CD4B and patatin (red, yellow & orange bars) only slightly enhanced protein levels compared to the GFP control. Silencing of AGP using a GBSS promoter and a convergent AGP promoter and GFP over-expression with the granule-bound starch synthase (GBBS) transit peptide (green bars) resulted in a significant increase in protein level, up to a 4- to 6-fold increase. Silencing of the rubisco (Rbcs) targeting peptide (blue bars) led to significant protein increase only in one line. Silencing of the ADP-glucose pyrophosphorylase (AGP) (grey bars) led to a significant increase of up to 3-fold in GFP content. These results clearly show that heterologous protein production in potato tubers can be significantly increased using the silencing, over-expression and targeting strategies according to the invention.

What is claimed is:

1. A method of producing a heterologous protein or peptide of interest, the method comprising the steps of:
   a. transforming a potato plant with an expression cassette, the expression cassette comprising (i) a nucleotide sequence capable of suppressing patatin expression; (ii) a nucleotide sequence capable of suppressing CD4B expression wherein the nucleotide sequence capable of suppressing CD4B comprises SEQ ID NO: 5 and SEQ ID NO: 6; (iii) a marker gene; and (iv) a gene coding for a heterologous protein or peptide of interest;
   b. cultivating the transformed potato plant; and
   c. extracting the heterologous protein or peptide of interest from the transformed potato plant.

2. The method of claim 1, wherein the nucleotide sequence capable of suppressing patatin expression comprises antisense and sense sequences of patatin as set forth in SEQ ID NO: 3 and SEQ ID: 4.

3. The method of claim 1, wherein the marker gene is selected from a group consisting of GFP, EGFP, GUS, LUX, CAH, SPT, NPTII, HPT, APHIV, BAR, PAT, CHS, AHAS, and flavonoid synthesis genes.

4. The method of claim 1, wherein the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

5. A method of producing a heterologous protein or peptide of interest, the method comprising the steps of:
   a. transforming a potato plant with an expression cassette, the expression cassette comprising (i) a nucleotide sequence capable of suppressing patatin expression; (ii) a nucleotide sequence capable of suppressing CD4B expression wherein the nucleotide sequence capable of suppressing CD4B comprises SEQ ID NO: 5 and SEQ ID NO: 6; (iii) a nucleotide sequence capable of overexpressing P19; (iv) a marker gene; and (v) a gene coding for a heterologous protein or peptide of interest;
   b. cultivating the transformed potato plant; and
   c. extracting the heterologous protein or peptide of interest from the transformed potato plant.

6. The method of claim 5, wherein the nucleotide sequence capable of suppressing patatin expression comprises antisense and sense sequences of patatin as set forth in SEQ ID NO: 3 and SEQ ID: 4; and wherein the nucleotide sequence capable of overexpressing P19 comprises the P19 sequence as set forth in SEQ ID NO: 2.

7. The method of claim 5, wherein the marker gene is selected from a group consisting of GFP, EGFP, GUS, LUX, CAH, SPT, NPTII, HPT, APHIV, BAR, PAT, CHS, AHAS, and flavonoid synthesis genes.

8. The method of claim 5, wherein the protein of interest is selected from a group consisting of interleukin-2, hirudin, insulin, interferons, lactoferrin, hemoglobin, erythropoietin, epidermal growth factor, anthrax vaccines, cholera vaccine, DPT vaccine, hib vaccine, hepatitis A vaccine, hepatitis B vaccine, hepatitis C vaccine, HPV vaccine, influenza vaccine, Japanese Encephalitis vaccine, MMR vaccine, MMRV vaccine, pneumococcal conjugate vaccine, pneumococcal polysaccharide vaccine, polio vaccine, rotavirus vaccine, smallpox vaccine, tuberculosis vaccine, typhoid vaccine, yellow fever vaccine, parvovirus vaccine, distemper vaccine, adenovirus vaccine, parainfluenza vaccine, bordetella vaccine, rabies vaccine, leptospirosis vaccine, lyme vaccine, corona vaccine, round/hookworm vaccine, dewormer vaccine, RNFN vaccine, and HIV vaccine.

\* \* \* \* \*

SEQUENCE LISTING

```
<160> NUMBER OF SEQ ID NOS: 12

<210> SEQ ID NO 1
<211> LENGTH: 1225
<212> TYPE: DNA
<213> ORGANISM: Solanum tuberosum

<400> SEQUENCE: 1
ataatctgca aatggcacta ctaaatattt tacaattta attttatga tgttagcaac      60 tactagttca acatttgcta cattgggaga aatggtgact gttcttagta ttgatggagg     120
tggaattaag ggaatcattc cggctaccat tctcgaattt cttgaaggac aacttcagga    180
agtggacaat aatacagatg caagacttgc agattacttt gatgtaattg gaggaacagg    240
tacaggaggt ttattgactg ctatgataac tactccaaat gaaaacaatc gacccttgc     300 tgctgctaaa gatattatac cttttacttt cgatcatggc cctaagattt ttgaacctag    360
tggttttcac cttgttgagc caaaatatga tggaaaatat cttatgcaag ttcttcaaga    420
aaaacttgga gaaactcgtg tgcatcaagc tttgacagaa gttgccatct caagctttga    480
catcaaaaca aataagccag taatattcac taagtcaaat ttagcaaaaa ctccagaatt    540
ggatgctaag atgtatgaca tatgttattc cacagcagca gctccaacat attttcctcc    600
acattacttt gctactaata ctagtaatgg agatcaatat gacttcaatc ttgttgatgg    660
cgatgttgct gctgttgatc cgtcgttatt atccattagc gttgcaacga gacttgcaca    720
```

```
agaggatcca gcatttgctt caattaagtc attgaattac aaacaaatgt tgttgctctc    780
attaggcact ggcactaatt cagagtttgc taaaaactat acagcagaag aggcagctaa    840
atggggtatt ctacaatgga tgtcacctt atgggaaatg agaagtgcag caagttctta    900
```
*(note: line at 900 as printed)*

```
catgaatgat tattaccttt ctactgtttt tcaagctctt gattcacaaa acaattacct    960
cagggttcaa gaaaatgcat taacaggcac agctactaca tttgatgatg cttctgtggc   1020
taatatgata ttattagtac aagttggtga aaacttattg aagaaatcag tttccgaaga   1080
caatcatgaa acctatgagg tagctctaaa gaggtttgca aaattgctct ctgataggaa   1140
gaaactccga gcaaacaaag cgtcttttta attcaaggtc tcgagttgtg ttagtaacct   1200
tactatgctt aattataagc gcttg                                         1225
```

<210> SEQ ID NO 2
<211> LENGTH: 519
<212> TYPE: DNA
<213> ORGANISM: Artificial Sequence
<220> FEATURE:
<223> OTHER INFORMATION: Binary vector

<400> SEQUENCE: 2

```
atggaacgag ctatacaagg aaacgacgct agggaacaag ctaacagtga acgttgggat     60
ggaggatcag gaggtaccac ttctcccttc aaacttcctg acgaaagtcc gagttggact    120
gagtggtggc tacataacga tgagacgaat tcgaatcaag ataatcccct tggtttcaag    180
gaaagctggg gtttcgggaa agttgtattt aagagatatc tcagatacga caggacggaa    240
gcttcactgc acagagtcct tggatcttgg acgggagatt cggttaacta tgcagcatct    300 cgattttcg gtttcgacca gatcggatgt acctatagta ttcggtttcg aggagttagt    360
```
*(cgattttcg as printed)*

```
atcaccgttt ctggagggtc gcgaactctt cagcatctct gtgagatggc aattcggtct    420
aagcaagaac tgctacagct tgccccaatc gaagtggaaa gtaatgtatc aagaggatgc    480
cctgaaggta ctgagacctt cgaaaaagaa agcgagtaa                           519
```

<210> SEQ ID NO 3
<211> LENGTH: 668
<212> TYPE: DNA
<213> ORGANISM: Solanum tuberosum

<400> SEQUENCE: 3

```
ggatcctctt gtgcaagtct cgttgcaacg ctaagggata taacgccgg atcaccaaca      60 gtagcaacac caccatcaac aagattgaac tcatatgtag caccattact agtatgagta    120
acaaagtgat gtggaggaaa atatattgga gctgctgctg tggaatagca tatgtcatac    180
atcttagcat ccaattctgg agactttgct aaatttgact tagtgaatat tactggctta    240
tttgttttta tgtcaaagct tgagatggca acttctgtca aagcttgatg cacacgagtt    300
tctccaagtt tttcttgaag aacttgcaga agatattttc catcatacct tgggccaaaa    360
attgaaccac tataattaaa aatatgaggg ccatgttcga agtaaaaggg tacaatatct    420
ttggcagcag caaagggtcg attgtttca tttggagtag ttatcatagc agtcaataaa    480
cctcctgtac ttgttcctcc aattacatca agtaatctg caagtcttgc atctttatta    540
ttgtccactt cctgaagttg tccttcaaga aattcgagaa tgatagccgg aatgattccc    600
ttaattccac ctccatcaat actaagaaca gtcaccattt cttccaactt agcacatgtt    660
gaacaatc                                                             668
```

<210> SEQ ID NO 4
<211> LENGTH: 525
<212> TYPE: DNA
<213> ORGANISM: Solanum tuberosum

<400> SEQUENCE: 4

```
gacttgcaga ttactttgat gtaattggag gaacaagtac aggaggttta ttgactgcta      60
tgataactac tccaaatgaa aacaatcgac cctttgctgc tgccaaagat attgtaccct     120
tttacttcga acatggccct catatttta attatagtgg ttcaattttt ggcccaaggt     180
atgatggaaa atatcttctg caagttcttc aagaaaaact tggagaaact cgtgtgcatc     240
aagctttgac agaagttgcc atctcaagct ttgacataaa aacaaataag ccagtaatat     300
tcactaagtc aaatttagca aagtctccag aattggatgc taagatgtat gacatatgct     360
attccacagc agcagctcca atatattttc ctccacatca ctttgttact catactagta     420
atggtgctac atatgagttc aatcttgttg atggtggtgt tgctactgtt ggtgatccgg     480
cgttattatc ccttagcgtt gcaacgagac ttgcacaaga ggatc                     525
```

<210> SEQ ID NO 5
<211> LENGTH: 240
<212> TYPE: DNA
<213> ORGANISM: Solanum lycopersicum

<400> SEQUENCE: 5

```
aacagcctca ttactctcac caaccattcg gatcacctga gtacggatgt tgctggggtc      60
agcacccaag ttttcaagga cacgggcagc cacaccttca ccttcacgta gcaatccaag     120
taacaagtgc tccgaaccaa tatagttatg ccctagctgg cgggcttcct ccagagagag     180
ttccagaaca cgcttggcac gagggtaaa agggatctca acagcaacga acccactacc     240
```

<210> SEQ ID NO 6
<211> LENGTH: 400
<212> TYPE: DNA
<213> ORGANISM: Solanum lycopersicum

<400> SEQUENCE: 6

```
acaagaagag gccagacgac ttggtcacaa ttttgttggc actgagcaga tcttgttggg      60
tctaattggt gagggaactg gtattgctgc caaggttctt aaatcgatgg ggatcaattt     120
gaaagatgct cgtgtggaag tggaaaagat aattggaagg ggtagtgggt tcgttgctgt     180
tgagatccct tttaccccctc gtgccaagcg tgttctggaa ctctctctgg aggaagcccg     240
ccagctaggg cataactata ttggttcgga gcacttgtta cttggattgc tacgtgaagg     300
tgaaggtgtg gctgcccgtg tccttgaaaa cttgggtgct gaccccagca acatccgtac     360
tcaggtgatc cgaatggttg gtgagagtaa tgaggctgtt                           400
```

<210> SEQ ID NO 7
<211> LENGTH: 720
<212> TYPE: DNA
<213> ORGANISM: Artificial Sequence
<220> FEATURE:
<223> OTHER INFORMATION: Binary vector

<400> SEQUENCE: 7

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
```

```
ctcgtgacca ccctgaccta cggcgtgcag tgcttcagcc gctacccga ccacatgaag      240 cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

<210> SEQ ID NO 8
<211> LENGTH: 231
<212> TYPE: DNA
<213> ORGANISM: Solanum tuberosum

<400> SEQUENCE: 8

```
atggcaagca tcacagcttc acaccacttt gtgtcaagaa gccaaacttc actagacacc       60
aaatcaacct tgtcacagat aggactcagg aaccatactc tgactcacaa tggtttaagg      120
gctgttaaca agcttgatgg gctccaatca agaactaata ctaaggtaac acccaagatg      180
gcatccagaa ctgagaccaa gagacctgga tgctcagcta ccattgtttg t                231
```

<210> SEQ ID NO 9
<211> LENGTH: 171
<212> TYPE: DNA
<213> ORGANISM: Pisum sativum

<400> SEQUENCE: 9

```
atggcttcta tgatatcctc ttccgctgtg caacagtca gccgtgcctc taggggggcaa       60 tccgccgcag tggctccatt cggcggcctc aaatccatga ctggattccc agtgaagaag      120
gtcaacactg acattacttc cattacaagc aatggtggaa gagtaaagtg c                171
```

<210> SEQ ID NO 10
<211> LENGTH: 788
<212> TYPE: DNA
<213> ORGANISM: Solanum tuberosum

<400> SEQUENCE: 10

```
ataatgcgtc cttcttcgtc aatcttcatg agaccgaatg cagtggcacg cttctcgtcc       60
attggcagtg cggcaacggt aatatcagca tctgtttctc tgtgggcttg aataaacttt      120
tcataatcca ttcgatacag atgatctcca gcaagtataa ggtattcaag aacagtatgc      180
tcctcaaaca accacagata ttgtctaaca gcatcagccg tgccctggaa ccaatcgggg      240
ttctctggac tttgttgagc cgcaagaact tccacaaagc cctcgttttt gtatcctccc      300
atattgctag catatgcccg tgaaaggtgg cgattcaggg aggcagagtt gaattgtgtg      360
agaacataga tcttggatat gttactgttc aagcaattgc ttacgggaat gtcaatcaga      420
cgataatttg ctccaagtgg aacgctggt tttgctcttt ttttagttag aggataaagt      480
cgggtcccag ctccacctcc aagaataatt cccaaaacac tccggctagc atctgggtct      540
agacatgtct gtgaattctg cgaatcagaa acagccttag gcgacataat caatggactt      600
cttctcacat tgaatcggac tcctttggaa cgtaacgacg acacaggcat caacttgtct      660
```

-continued

```
ccggcgagat gagaagacga aaatgagaga tttctgctgg atactgcacg tgtagaatca    720
tttcttctct cattgatgca attgttagaa gaaggtgaag attttaacgc tccaatggaa    780
gccgccat                                                             788

<210> SEQ ID NO 11
<211> LENGTH: 599
<212> TYPE: DNA
<213> ORGANISM: Solanum tuberosum

<400> SEQUENCE: 11
agtccattga ttatgtcgcc taaggctgtt tctgattcgc agaattcaca gacatgtcta     60
gacccagatg ctagccggag tgttttggga attattcttg gaggtggagc tgggacccga    120
ctttatcctc taactaaaaa aagagcaaag ccagccgttc cacttggagc aaattatcgt    180
ctgattgaca ttcccgtaag caactgcttg aacagtaaca tatccaagat ctatgttctc    240
acacaattca actctgcctc tctgaatcgc cacctttcac gggcatatgc tagcaacatg    300
ggaggataca aaaacgaggg ctttgtggaa gttcttgctg ctcaacaaag tccagagaac    360
cccgattggt tccagggcac ggctgatgct gtcagacaat atctgtggtt gtttgaggag    420
catactgttc ttgaatacct tatactcgct ggagatcatc tgtatcgaat ggattatgaa    480
aagtttattc aagcccacag agaaacagat gctgatatta ccgttgccgc actgccaatg    540
gacgagaagc gtgccactgc attcggtctc atgaagattg acgaagaagg acgcattat     599

<210> SEQ ID NO 12
<211> LENGTH: 6
<212> TYPE: PRT
<213> ORGANISM: Artificial Sequence
<220> FEATURE:
<223> OTHER INFORMATION: microsomal retention signal

<400> SEQUENCE: 12

Ser Glu Lys Asp Glu Leu
1               5
```